(12) United States Patent
Van Der Kooy et al.

(10) Patent No.: US 7,211,434 B2
(45) Date of Patent: May 1, 2007

(54) PRIMITIVE NEURAL STEM CELLS AND METHOD FOR DIFFERENTIATION OF STEM CELLS TO NEURAL CELLS

(76) Inventors: Derek Van Der Kooy, 144 MacPherson Avenue, Toronto, Ontario (CA) M5R 1W8; Vincent Tropepe, 56 Charlesgate East, Apt. 132, Boston, MA (US) 02215

(*) Notice: Subject to any disclaimer, the term of this patent is extended or adjusted under 35 U.S.C. 154(b) by 472 days.

(21) Appl. No.: 09/966,768

(22) Filed: Sep. 28, 2001

(65) Prior Publication Data

US 2002/0164791 A1 Nov. 7, 2002

Related U.S. Application Data

(60) Provisional application No. 60/236,394, filed on Sep. 29, 2000.

(51) Int. Cl.
C12N 5/02 (2006.01)
C12N 5/06 (2006.01)
(52) U.S. Cl. .................. 435/377; 435/325; 435/375
(58) Field of Classification Search ............. 435/325, 435/375, 29; 514/44; 424/93.1
See application file for complete search history.

(56) References Cited

U.S. PATENT DOCUMENTS 5,942,435 A * 8/1999 Wheeler .................... 435/325

FOREIGN PATENT DOCUMENTS

| WO | WO 99/01159 A | 1/1999 |
| WO | WO 99/01553 A | 1/1999 |
| WO | WO 99/32606 A | 7/1999 |
| WO | WO 01/51616 A2 | 7/2001 |

OTHER PUBLICATIONS

Society of Neuroscience Abstracts, 1999, vol. 25, pp. 527.*
Okabe et al., Dvelopment of neuronal precursor cells and functional postmitotic neurons from embryonic stem cells in virto, 1996, Mechanisms of Development, vol. 59, pp. 89-102.*
Fraichard et al., In virto differentiation of embyronic stem cells into glial cells and functional neurons, 1995, Journal of Cell Science, vol. 108, pp. 3181-3188.*
Tropepe et al., Direct neural fate specification from embryonic stem cells: A primitive mammlian neural stem cell stage acquired through a default mechanism, 2001, Neuron, vol. 30, pp. 65-78.*
Weissmann, Translating stem and progenitor cell biology to the clinic: Barriers and opportunities, 2000, SCIENCE, vol. 287, pp. 1442-1446.*
Donovan et al., The end of the beginning for pluripotent stem cells, 2001, NATURE, vol. 414, pp. 92-97.*
Brustle et al. Embryonic stem cell-derived glial precursors: a source of myelinating transplants.Science. Jul. 30, 1999;285(5428):754-6.*
McDonald et al. Transplated embryonic stem cells survive, differentiate and promote recovery in injured rat spinal cord. Nat Med. Dec. 1999;5(12):1410-2.*
Yang et al. Neural stem cells spontaneously express dopaminergic traits after transplantation into the intact or 6-hydroxydopamine-lesioned rat. Exp Neurol. Sep. 2002;177(1):50-60.*
Benninger et al. Differentiation and histological analysis of embryonic stem cell-derived neural transplants in mice. Brain Pathol. Jul. 2000;10(3):330-41.*
Neophytou et al. Muller-cell-derived leukaemia inhibitory factor arrests rod photoreceptor differentiation at a postmitotic pre-rod stage of development. Development. Jun. 1997;124(12):2345-54.*
Stem Cells: Scientific Progress and Future Research Directions. "Chapter 2. The Embryonic Stem Cell", Department of Health and Human Services. Jun. 2001. http://stemcells.nih.gov/info/scireport/chapter1.asp.*
Dinsmore et al. Embyronic stem cells as a model for studying regulation of cellular□□differentiation. Theriogenology. Jan. 1, 1998;49(1):145-51.*
Humphrey et al. Maintenance of pluripotency in human embryonic stem cells is STAT3 independent.□□Stem Cells. 2004;22(4):522-30.*
Sato et al. Maintenance of pluripotency in human and mouse embryonic stem cells through□□activation of Wnt signaling by a pharmacological GSK-3-specific inhibitor. Nat Med. Jan. 2004;10(1):55-63.*
Y. Benninger et al. "Differentiation and Histological Analysis of Embryonic Stem Cell-Derived Neural Transplants in Mice." Brain Pathology 10 pp. 330-341 (2000).
I L. Weissmann. Translating Stem and Progenitor Cell Biology to the Clinic: Barriers and Opportunities. Science, vol. 287, Feb. 25, 2000.
P.J. Donovan & J. Gearhart. "The end of the beginning for pluripotent stem cells." Nature, vol. 414, Nov. 1, 2001, pp. 92-97.
C.H. Waddington and G.A. Schmidt. "Induction by Heteroplastic Grafts of the Primitive Streak in Birds." Roux's Arch. EntwMech. Org. 128, (1933) pp. 522-563.
G. R. Martin et al. "The Development of Cystic Embryoid Bodies in Vitro from Clonal Teratocarcinoma Stem Cells." Developmental Biology 61, pp. 230-244 (1977).
R.S.P Beddington and E.J. Robertson. "An assessment of the developmental potential of embryonic stem cells in the midgestation mouse embryo." Development 105, (1989) pp. 733-737.
J.M. Oppenheimer. "Structures Developed in Amphibians by Impantation of Living Fish Organizer." Proc. Soc. Exp. Biol. Med 34, (1936) pp. 461-463.

(Continued)

Primary Examiner—Daniel M. Sullivan
(74) Attorney, Agent, or Firm—Dann, Dorfman, Herrell & Skillman; Kathleen D. Rigaut; Robert C. Netter, Jr.

(57) ABSTRACT

Described are a novel cell type in the neural lineage, and method of producing the same based on the degree of neural commitment and growth factor responsiveness in vitro and the potential to give rise to neural and non-neural progeny in vivo. The novel vell type of neural lineage and cells derived therefrom have a number of applications including applications regarding tissue engineering, transplantation and gene therapy and drug discovery. Also described are suggested uses of the method and cell type including isolating genes that positively and negatively regulate the transition from an ES cell to a neural cell and generally for studying ES cell models of mammalian neural development.

29 Claims, 7 Drawing Sheets

OTHER PUBLICATIONS

M.V. Miles and B. M. Johansson. "Analysis of Factors Controlling Primary Germ Layer Formation and Early Hematopoiesis Using Embryonic Stem Cell in Vitro Differentiation." Leukemia 11 (S3)m (1997) pp. 454-456.

B.A. Reynolds et al. "A Multipotent EGF-Responsive Striatal Embryonic Progenitor Cell Produces Neurons and Astrocytes." The Journal of Neuroscience, Nov. 1992 12(11), pp. 4565-4574.

J. Nichols et al. "Derivation of Germline Competent Embryonic Stem Cells with a Combination of Interleukin-6 and Soluble Interleuken-6 Receptor." Experimental Cell Research 215, pp. 237-239 (1994).

M.J. Evans and M.H. Kaufman. "Establishment in culture of pluripotential cells from mouse embryos." Nature, vol. 292. Jul. 9, 1981, pp. 154-156.

A. Nagy and J. Rossant. "Production of completely ES cell-derived fetuses." In Gene targeting: a practical approach (ed. A.L. Joyner), pp. 147-179, IRL Press, Oxford, UK.

C.G. Bellows and J.E. Aubin. "Determination of Numbers of Osteoprogenitors Present in Isolated Fetal Rat Calvaria Cells *In Vitro*." Developmental Biology 133, pp. 6-13 (1989).

H. Kawasaki et al. "Induction of midbrain dopaminerigc neurons from ES cells by stromal cell-derived inducing activity." Neuron 28, pp. 31-40.

J.J. Otero et al. "Cell-cell contact regulates commitment by cultured embryonic stem cells." Society for Neuroscience Abstracts, vol. 27, No. 1, p. 341, 2001.

S. Taraviras et al. "Characterization of the mouse HNF-4 gene and its expression during mouse embryogenesis." Mechanisms of Development 48 (1994) pp. 67-79.

M. Li et al. "Essential function of LIF receptor in motor neurons." Nature, vol. 378, Dec. 14, 1995, pp. 724-727.

Y. Nakamura et al. "The bHLH Gene *Hes1* as a Repressor of the Neuronal Commitment of CNS Stem Cells." The Journal of Neuroscience, Jan. 1, 2000, 20(1) pp. 283-293.

D. Martens et all. "Separate Proliferation Kinetics of Fibroblast Growth Factor-Responsive and Epidermal Growth Factor-Responsive Neural Stem Cells within the Embryonic Forebrain Germinal Zone." The Journal of Neuroscience, Feb. 1, 2000, 20(3), pp. 1085-1095.

A. Fainsod et al. "The dorsalizing and neural inducing gene *follistatin* is an antagonist of *BMP-4*." Mechanisms of Development 63 (1997), pp. 39-50.

S. Weiss et al. "Is there a neural system cell in the mammalian forebrain?" TINS vol. 19, No. 9, 1996, pp. 367-393.

R. Harland and J. Gerhart. "Formation and Function of Spemann's Organizer." Annu. Rev. Cell Dev. Biol., 1997, 13 pp. 611-667.

J. Conover et al. "Ciliary neurotrophic factor maintains the pluripotentiality of embryonic stem cells." Development 119, pp. 559-565 (1993).

G. R. Martin. "Isolation of a pluripotent cell line from early mouse embryos cultured in medium conditioned by teratocarcinoma stem cells." Proc. Natl. Acad. Sci. USA, vol. 78, No. 12, pp. 7634-7638, Dec. 1981.

A. Nagy et al. "Derivation of completely cell culture-derived mice from early-passage embryonic stem cells." Proc. Natl. Acad. Sci. USA, vol. 90, No. 18, pp. 8424-8428, Sep. 1993.

T. Lamb et al. "Neural Induction by the Secreted Polypeptide Noggin." Science vol. 262, Oct. 29, 1993, pp. 713-718.

B. Reynolds and S. Weiss. "Generation of Neurons and Astrocytes from Isolated Cells of the Adult Mammalian Central Nervous System." Science, vol. 255, pp. 1707-1710, Mar. 1992.

D. van der Kooy and S. Weiss. "Why Stem Cells?" Science vol. 287, Feb. 25, 2000, pp. 1439-1441.

R. L. Williams et al. "Myeloid leukaemia Inhibitory factor maintains the developmental potential of embryonic stem cells." Nature vol. 336, Dec. 15, 1988, pp. 684-687.

D. G. Wilkinson et al. "Segmental expression of Hox-2 homoeobox-containing genes in the developing mouse hindbrain." Nature vol. 341, Oct. 5, 1989, pp. 405-409.

W. S. Smith et al. "Segmented noggin protein mimics the Spemann organizer in dorsalizing *Xenopus* mesoderm." Nature vol. 361, Feb. 11, 1993, pp. 547-549.

A. Simeone et al. "Nested expression domains of four homeobox genes in developing rostral brain." Nature vol. 358, Aug. 20, 1992, pp. 687-690.

Y. Sasai et al. "Regulation of neural induction by the Chd and Bmp-4 antagonistic patering signals in *Xenopous*." Nature vol. 376, Jul. 27, 1995, pp. 333-338.

A. Hemmati-Brivanlou & D. A. Melton. "A truncated activin receptor inhibits mesoderm induction and formation of axial structures in *Xenopous* embryos." Nature vol. 359, Oct. 15, 1992, pp. 609-614.

P. A. Hoodless and A. Hemmati-Brivanlou. "Inhibitory control of neural differentiation in mammalian cells." Dev. Genes Evol (1997) 207 pp. 19-28.

P.A. Wilson et al. "Concentration-dependent pattering of the *Xenopous* ectoderm by BMP4 and its signal transducer Smad1." Development 124, pp. 3177-3184 (1997).

G. Oliver et al. "*Six3*, a murine homologue of the sine *oculis* gene, demarcates the most anterior border of the developing neural plate and is expressed during eye development." Development 121, pp. 4045-4055 (1995).

Y. Grinblat et al. "Determination of the zebrafish forebrain: induction and patterning." Development 125, pp. 4403-4416 (1998).

J. L. de la Pompa et al. "Conservation of the Notch signaling pathway in mammalian neurogenesis." Development 124, pp. 1139-1148 (1997).

B. G. Ciruna et al. "Chimeric analysis of *fibroblast growth factor receptor-1(Fgfr1)* function: a role for FGFR1 in morphogenetic movement through the primitive streak." Development 124, pp. 2829-2841 (1997).

D. Acampora et al. "Visceral endoderm-restricted translation of *Otx 1* mediates recovery of *Otx2* requirements for specification of anterior neural plate and normal gastrulation." Development 125, pp. 5091-5104 (1998).

R.S.P Beddington "Induction of a second neural axis by the mouse node." Development 120, pp. 613-620, (1994).

R.S.P. Beddington et al. "*Brachyury*—a gene affecting mouse gastrulation and early organogenesis." Development 1992 Supplement, pp. 157-165 (1992).

T.P. Yamaguchi et al. "*fgfr-1* is required for embryonic growth and mesodermal patterning during mouse gastrulation" Genes & Development 8, pp. 3032-3044, 1994.

J. Li et al. "Mammalian hepatocyte differentiation requires the transcription factor HNF-4α." Genes & Development 14, pp. 464-474, 2000.

S. Hoppler et al. "Expression of a dominant-negative Wht blocks induction of MyoD in *Xenopus* embryos." Genes & Development 10, pp. 2805-2817, 1996.

G. Friedrich and P. Sorlano. "Promoter traps in embryonic stem cells: a genetic screen to identify and mutate developmental genes in mice." Genes & Development 5, pp. 1513-1523, 1991.

V. Tropepe et al. "Distinct Neural Stem Cells Proliferate in Response to EGF and FGF in the Developing Mouse Telencephalon." Developmental Biology 208, pp. 166-188, 1999.

B.A. Reynolds and S. Weiss. "Clonal and Popluation Analyses Demonstrate That an EGF-Responsive Mammalian Embryonic CNS Precursor Is a Stem Cell." Developmental Biology 175, pp. 1-13, 1996.

J.L. Wrana. "Regulation of Smad Activity." *Cell*, vol. 100, pp. 189-192, Jan. 21, 2000.

U. Lendahl et al. "CNS Stem Cells Express a New Class of Intermediate Filament Protein." Cell, vol. 60, pp. 585-595, Feb. 23, 1990.

G. Bain et al. "Embryonic Stem Cells Express Neuronal Properties *in Vitro*." Developmental Biology 168, pp. 342-357 (1995).

S. Okabe et al. "Developmental of neuronal precursor cells and functional postmitotic neurons from embryonic stem cells in vitro." Mechanisms of Development 59 (1996), pp. 89-102.

S. Piccolo et al "Dorsoventral Patterning in Xenopus: Inhibition of Ventral Signals by Direct Binding of Chordin to BMP-4." Cell, vol. 86, pp. 589-598, Aug. 23, 1996.

L.B. Zimmerman et al. "The Spermann Organizer Signal noggin Binds and Inactivates Bone Morphogenetic Protein 4." Cell, vol. 86, 599-606, Aug. 23, 1996.

E. Coucouvanis and G.R. Marin. "BMP singaling plays a role in visceral endoderm differentiation and cavitation in the early mouse embryo." Development 126, pp. 535-546, (1999).

S. Piccolo et al. "The head inducer Cerberus is a multifunctional antagonist of Nodal, BMP and Wnt signals." Nature vol. 397, Feb. 25, 1999, pp. 707-710.

J.J.H. Pearce et al. "A Mouse Cerberus/Dan-Related Gene Family." Developmental Biology 209, pp. 98-110 (1999).

A. Streit and C D. Stern. "Neural induction a bird's eye view." TIG, Jan. 1999, vol. 15, No. 1, pp. 20-24.

A. Streit et al. "Chordin regulates primitive streak development and the stability of induced neural cells, but is not sufficient for neural induction in the chick embryo." Development 125, pp. 507-519 (1998).

H. Grunz and L. Tacke. "Neural differentiation of *Xenopus laevis* ectoderm takes place after disaggregation and delayed reaggregation without inducer." Cell Differentiation and Development, 28 (1989), pp. 211-218.

C. Sirard et al. "The tumor suppressor gene *Smad4/Dpc4* is required for gastrulation and later for anterior development of the mouse embryo." Genes & Development 12, pp. 107-119, 1998.

J. A. Belo et al. "*Cerberus-like* is a secreted factor with neuralizing activity expressed in the anterior primitive endoderm of the mouse gastrula." Mechanisms of Development 68 (1997) pp. 45-57.

S. M. Sato and T. D. Sargent. "Development of Neural Inducing Capacity in Dissociated *Xenopus* Embyros." Developmental Biology 134, pp. 263-266 (1989).

B. M. Johansson and M. V. Wiles. "Evidence for Involvement of Activin A and Bone Morphogenetic Protein 4 in Mammalian Mesoderm and Hematopoietic Development." Molecular and Cellular Biology, Jan. 1995, pp. 141-151.

P. A. Wilson and A. Hemmati-Brivanlou. "Induction of epidermis and inhibition of neural fate by Bmp-4." Nature, vol. 376, Jul. 27, 1995, pp. 331-336.

S.F. Godsave and J.M. W. Slack. "Single cell analysis of mesoderm formation in the Xenopus embryo." Development 111, pp. 523-530 (1991).

A. Glinka et al. "Head induction by simultaneous repression of Bmp and Wnt signaling in *Xenopus*." Nature, vol. 389, Oct. 2, 1997, pp. 517-519.

A. Hemmati-Brivanlou and D. Melton. "Vertebrate Neural Induction." Annu. Rev. Neurosci., 1997, 20, pp. 43-60.

M. F. A. Finley et al. "BMP-4 Inhibits Neural Differentiation of Murine Embryonic Stem Cells." Jon Wiley & Sons, Inc. J. Neurobiol 40, pp. 271-287, 1999.

D. Bachiller et al. "The organizer factors Chordin and Noggin are required for mouse forebrain development." Nature, vol. 403, Feb. 10, 2000, pp. 658-661.

T. Bouwmeester et al. "Cerberus is a head-inducing secreted factor expressed in the anterior endoderm of Sepmann'organizer." Nature, vol. 382, Aug. 15, 1996, pp. 595-601.

T. Tohyama et al. "Nestin Expression in Embryonic Human Neuroepithelium and in Human Neuroepithelial Tumor Cells." Laboratory Investigation, vol. 66, No. 3, pp. 303-313, 1992.

S. Fedoroff et al. "Microglia and Astroglia Have a Common Progenitor Cell." Journal of Neuroscience Research 50, pp. 477-486 (1997).

I. L. Weissman. "Stem Cells: Units of Development, Units of Regeneration, and Units in Evolution." Cell, vol. 100, pp. 157-168, Jan. 7, 2000.

S.J. Morrison et al. "Regulatory Mechanisms in Stem Cell Biology." Cell, vol. 88, pp. 287-298, Feb. 7, 1997.

A. Simeone et al. "Two vertebrate homeobox genes related to the *Drosophila empty spiracles* gene are expressed in the embryonic cerebral cortex." The EMBO Journal, vol. 11, No. 7, pp. 2541-2550, 1992.

C.S. Potten and M. Loeffler. "Stem cells: attributes, cylces, spirals, pitfalls and uncertainties. Lessons for and from the Crypt." Development 110, pp. 1001-1020 (1990).

D.L. Clarke et al. "Generalized Potential of Adult Neural Stem Cells." Science, vol. 288, pp. 1660-1663, Jun. 2, 2000.

A. Hemmati-Brivanlou and D. A. Melton. "Inhibition of Activin Receptor Signaling Promotes Neuralization in Xenopous." Cell, vol. 77, pp. 273-281, Apr. 22, 1994.

R. S. P. Beddington and E. J. Robertson. "Axis Development and Early Asymmetry in Mammals." Cell, vol. 96, pp. 195-209, Jan. 22, 1999.

A. G. Smith et al. "Inhibition of pluripotential embryonic stem cell differentiation by purified polypeptides." Nature, vol. 336, Dec. 15, 1988, pp. 688-690.

C. Strubing et al. "Differentiation of pluripotent embryonic stem cells into the neuronal lineage in vitro gives rise to mature inhibitory and excitatory neurons." Mechnanisms of Development 53 (1995) pp. 275-287.

A. Fraichard et al. "In vitro differentiation of embryonic stem cells into glial cells and functional neurons." Journal of Cell Science 108, pp. 3181-3188 (1995).

W. L. Stanford et al. "Expression Trapping: Identification of Novel Genes Expressed in Hematopoietic and Endothelial Lineages by Gene Trapping in ES Cells." Blood, vol. 92, No. 12, Dec. 15, 1998, pp. 4622-4631.

J. Nichols et al. "Formation of Pluripotent Stem Cells in the Mammalian Embryo Depends on the POU Transcriptions Factor Oct. 4." Cell, vol. 95, pp. 379-391, Oct. 30, 1998.

U. Koshimizu et al. "Functional requirement of gp130-mediated signaling for growth and survival of mouse primordial germ cells in vitro and derivation of embryonic germ (EG) cells." Development 122, pp. 1235-1242, (1996).

C. Dani et al. "Paracrine Induction of Stem Cell Renewal by LIF-Deficient Cells: A New ES Cell Regulatory Pathway." Developmental Biology 203, pp. 149-162 (1998).

A. G. Elefanty et al. "Hematopoietic-Specific Genes Are Not Induced During in Vitro Differentiation of *scl*-Null Embryonic Stem Cells." Blood, vol. 90, No. 4, Aug. 15, 1997; pp. 1435-1447.

R. J. Arceci, et al. "Mouse GATA-4: a Retinoic Acid-Inducible GATA-Binding Transcription Factor Expressed in Endodermally Derived Tissues and Heart." Molecular and Cellular Biology, Apr. 1993, pp. 2235-2246.

O. Brüstle et al. "Embryonic Stem Cell-Derived Glial Precursors: A Source of Myelinating Transplants." Science, vol. 285, Jul. 30, 1999, pp. 754-756.

M.George-Weinstein et al. "Skeletal Myogenesis: The Preferred Pathway of Chick Embryo Ephiblast Cells *in Vitro*." Developmental Biology 173, pp. 279-291 (1996).

A-K. Hadjantonakis et al. "Generating green fluorescent mice by germline transmission of green fluorescent ES cells." Mechanisms of Development 76, (1998), pp. 79-90.

M. F. Mehler and J.A. Kessler. "Hematolymphopoietic and inflammatory cytokines in neural development." TINS, vol. 20, No. 8, 1997, pp. 357-365.

T.C. Doetschman et al. "The *in vitro* development of blastocyst-derived embryonic stem cell lines: formation of visceral yolk sac, blood islands and myocardium." J. Embryol. exp. Mroph. 87, pp. 27-45, (1985).

T. Kishimoto et al. "Cytokine Signal Transduction." Cell, vol. 76, pp. 253-262, Jan. 28, 1994.

E. Coucouvanis and G. R. Martin. "Signals for Death and Survival: A Two-Step Mechanism for Cavitation in the Vertebrate Embryo." Cell, vol. 83, pp. 279-287, Oct. 20, 1995.

B. J. Chiasson et al. "Adult mammalian forebrain ependymal and subependymal cells demonstrate proliferative potential but only subependymal cells have neural stem cell characteristics." J. Neurosci. 19, pp. 4462-4471.

K.S. O'Shea. "Embryonic stem cell models of development." Anat. Rec. (New Anat.) 257, 32-41, 1999.

R.M. Seaberg et al. "Neural determination genes revealed by expression trapping in embryonic stem cells." Soc., Neurosci. Abst. 25, p. 527, 1999.

J. Yamashita et al. "Flk1-positive cells derived from embryonic stem cells serve as vascular progenitors." Nature, vol. 408, pp. 92-96, Nov. 2, 2000.

J W. McDonald et al. "Transplanted embryonic stem cells survive, differentiate and promote recovery in injured rat spinal cord." Nature Medicine, vol. 5, No. 12, pp. 1410-1412, Dec. 1999.

M. Yang et al. "Neural Stem Cells Spontaneously Express Dopaminergic Traints after Transplantation into the Intact or 6-Hydroxydopamine-Lesioned Rat." Experimental Neurology, vol. 177, pp. 50-60, 2002.

S. Weiss et al. "Multipotent CNS Stem Cells Are Present in the Adult Mammalian Spinal Cord and Venticular Neuroaxis." The Journal of Neuroscience, Dec. 1, 1996, 16(3) pp. 7599-7609.

V. Tropepe et al. "Autonomous neural cell fate specification in mouse embryonic stem cells." Poster at Meeting of the Society for Neuroscience, Miami Beach, Florida, Oct. 23-28, 1999.

* cited by examiner

PRIMITIVE NEURAL STEM CELLS AND METHOD FOR DIFFERENTIATION OF STEM CELLS TO NEURAL CELLS

RELATED APPLICATIONS

This application claims priority from U.S. Provisional patent application No. 60/236,394 filed Sep. 29, 2000, entitled "Primitive Neural Stem Cells And Method For Differentiation Of Stem Cells To Neural Cells".

FIELD OF THE INVENTION

This invention is in the field of cellular differentiation, more particularly to differentiation of stem cells to neural cells, to novel primitive neural cells and to methods of differentiation and uses thereof.

BACKGROUND OF THE INVENTION

Neural stem cells have a fundamental role in generating cellular diversity in the developing mammalian nervous system. However, there is very little known about how neural stem cells are formed initially in embryogenesis. Evidence from studies primarily in Xenopus suggest that the acquisition of a neural fate in ectoderm cells is actively repressed and that escaping the repressive signal is the predominant mechanism by which cells reveal their default neural identity (Hemmati-Brivanlou and Melton, 1997). However, it is uncertain whether default neural specification occurs in mammalian development, and if so whether the process of default neural fate specification is homologous among vertebrate species.

During mouse gastrulation cells derived from the embryonic ectoderm are organized into either neural or epidermal primordia. The concept of vertebrate neural induction, borne out of studies in amphibian embryology, was proposed to account for the segregation of these two vertebrate ectodermal lineages (Spemann and Mangold, 1924; Waddington and Schnidt, 1933; Oppenheimer, 1936; Beddington, 1994). It was postulated that the nascent embryonic ectoderm received a positive inducing signal from the dorsal organizer tissue during gastrulation, which caused the ectodermal cells to adopt a neural fate in a restricted manner. In the absence of this signal, ectodermal cells were presumed to differentiate into epidermis, independent of any cellular communication.

Results from in vitro experiments of isolated ectodermal (animal cap) cells derived from amphibian gastrula supported a different model for neural fate specification. Prolonged low-density dissociation of ectodermal cells, in the absence of organizer tissue, resulted in most of the cells expressing neural marker or forming neural structures upon reaggregation (Godsave and Slack, 1989; Grunz and Tacke, 1989; Sato and Sargent, 1989). Furthermore, ectodermal explants (undissociated cells (expressing a dominant-negative receptor for activin (a member of the TGFβ superfamily of growth factors) were shown to become neural when cultured in vitro (Hemmati-Brivanlou and Melton, 1994). In studies aimed at identifying the nature of the organizer signals, molecules isolated from mesendodermal tissue, such as noggin and chordin, were found to be sufficient for inducing a second neural axis in analogous ectopic experiments performed in Xenopus (Smith et al., 1993; Sasai et al., 1995). However, the biochemical mechanism by which organizer signals promoted neural differentiation of ectodermal cells was not entirely consistent with a positive induction model for neural fate determination. Noggin and chorein were shown to act by binding extracellularly to bone morphogenetic proteins (BMPs), members of the TGFβ superfamily of molecules that strongly inhibit neural differentiation (Hemmati-Brivanlou and Melton, 1994). Thus, in a restricted manner, noggin and chordin prevent the binding of BMPs to their cognate receptors expressed on the surface of ectodermal cells (Piccolo et al., 1996; Zimmerman et al., 1996). In fact, BMP4 was shown to act as a positive signal for epidermal fate determination in the Xenopus ectoderm (Wilson and Hemmati-Brivanlou, 1995). These findings from amphibian experiments were consistent with the notion that the establishment of neural identity from the uncommitted ectoderm occurs by default (i.e. a state achieved autonomously after the removal of the inhibitory signals) in the absence of neural-inducing factors emanating from the organizer.

Embryonic stem (ES) cells are precursors to all embryonic lineages. ES cells are derived from the inner cell mass (ICM) of the pre-implanation mouse embryo (Evans and Kaufman, 1981; Martin, 1981) and can be sustained in an undifferentiated state in vitro while maintaining ICM characteristics. In prior studies of the neuronal differentiation of embryonic stem (ES) cells each experiment was preceded by embryoid body (EB) formation in the presence of serum. As a result, the derivation of neural cells was accomplished indirectly and under conditions where many culture media parameters are unknown.

It is desirable to have a method for differentiating ES cells toward neural cells more directly. Furthermore, it is desirable to have a model system with known constituents and well defined end products for the differentiation of neural cells from ES cells. Such as system would be useful in analyzing the role of single genes in the regulation of neural development, and for the development and testing of drugs for the treatment of developmental and cerebral neural anomalies and neuropathies.

SUMMARY OF THE INVENTION

The present invention concerns a novel primitive neural stem cell and associated methods for differentiating embryonic stem cells toward neural cells under completely defined media conditions, and methods of use of the new stem cell and methods of differentiation.

In accordance with the present invention, it has surprisingly been discovered that in low-density cell culture assays, in the absence of serum derived or feeder cell-derived factors and in the absence of embryoid body (EB) formation, ES cells directly differentiate into neural cells. The transition from ES cell to neural cell can be enhanced by the inhibition of TGFβ-related signaling, in a manner that is consistent with a default model of neural fate specification, but one which is distinct from Xenopus default neuralization. Furthermore, the present invention describes a previously unidentified primitive neural stem cell stage in the neural lineage, which defines the transition between ES cell and neural stem cell.

Accordingly, in its broad aspect the present invention provides a novel primitive neural stem cell; this cell being characterized in that it defines the transition between ES cell and neural stem cell.

According to one embodiment of the present invention there is provided one or more cells expressing one or more neural precursor cell marker(s), preferably nestin, and one or more neural specific mRNA molecule(s), preferably Emx2 and/or HoxB1, and having multilineage potential.

In another broad aspect, the present invention provides a method for differentiating one or more pluripotent embryonic stem (ES) cell(s) toward neural cells. According to one embodiment the method comprises: a) obtaining ES cells and serum-free media; b) culturing the ES cells at low density in the serum-free media, preferably the ES cells are cultured at a density of greater than zero and less than about 50 cells/µl, more preferred between about 1 cell/µl and about 50 cells/µl, even more preferably the ES cells are cultured at a density of 20 or fewer cells/µl; and most preferably at a density of 10 or fewer cells/µl (but greater than 0 cells/µl) and c) allowing said ES cell(s) to differentiate toward the neural cell(s).

According to another embodiment of the present invention provides a method for differentiating one or more pluripotent embryonic stem (ES) cell(s) toward neural cells the method comprising: a) obtaining ES cells and serum-free media wherein a cytokine is added to the media, preferably the cytokine is leukemia inhibitory factor (LIF); b) culturing the ES cells at low density in the serum-free media, preferably the ES cells are cultured at a density greater than zero and less than about 50 cells/µl, more preferred between about 1 cell/µl and about 50 cells/µl, even more preferably the ES cells are cultured at a density of 20 or fewer cells/µl; and most preferably at a density of 10 or fewer cells/µl (but greater than 0 cells/µl); and c) allowing said ES cell(s) to differentiate toward the neural cell(s).

According to yet another embodiment the present invention provides a method for differentiating one or more pluripotent embryonic stem (ES) cell(s) toward neural cell(s) the method comprising: (a) obtaining ES cells and serum-free media wherein one or more cytokines is/are added to the media, preferably the cytokine is leukemia inhibitory factor (LIF), and one or more growth factors is/are added to the media, preferably the growth factor is selected from the members of the fibroblast growth factor (FGF) family of growth factors, more preferably the growth factor is FGF2; (b) culturing the ES cells at low density in the serum-free media, preferably the ES cells are cultured at a density preferably the ES cells are cultured at a density between about 1 cell/µl and about 50 cells/µl, more preferably the ES cells are cultured at a density of 20 cell/µl; and (c) allowing said ES cell(s) to differentiate toward the neural cell(s).

In another embodiment according to the present invention there is provided a method for differentiating one or more pluripotent embryonic stem (ES) cell(s) toward neural cell(s) the method comprising: (a) obtaining ES cells and serum free media, preferably wherein one or more cytokines is/are added to the media, preferably the cytokine is leukemia inhibitory factor (LIF), preferably one or more growth factors is/are also added to the media, preferably the growth factor is selected from the members of the fibroblast growth factor (FGF) family of growth factors, more preferably the growth factor is FGF2; (b) culturing the ES cells at low density in the serum-free media, preferably the ES cells are cultured at a density greater than zero and less than about 50 cells/µl, more preferred between about 1 cell/µl and about 50 cells/µl, even more preferably the ES cells are cultured at a density of 20 or fewer cells/µl; and most preferably at a density of 10 or fewer cells/µl (but greater than 0 cells/µl); and (c) allowing said ES cell(s) to differentiate toward the neural cell(s).

In one embodiment of the methods of the invention an inhibitor of TGF-β-related signaling is administered to the media, preferably the inhibitor is the protein Noggin. In yet another embodiment of the method of the invention the inhibitor is selected from among the *Cerberus* family of proteins.

In another aspect, the present invention provides a method for producing secondary neural stem cell colonies. According to one embodiment, the method comprises: (a) culturing ES cells in low cell density completely defined serum-free media for a sufficient time and under appropriate conditions to allow differentiation of the ES cells; (b) dissociating and subcloning primary neural cell colonies generated from the said ES cells; and (c) administering a growth factor to the dissociated neural cells, preferably the growth factor is selected from among the members of the fibroblast growth factor (FGF) family of growth factors, more preferably the growth factor is FGF2.

According to another embodiment the present invention provides a method for producing secondary neural stem cell colonies the method comprising: (a) culturing ES cells in low cell density completely defined serum-free media for a sufficient time and under appropriate conditions to allow differentiation of the ES cells; (b) dissociating and subcloning primary neural cell colonies generated from the said ES cells; and (c) administering a growth factor to the dissociated neural cells, preferably the growth factor is selected from among the members of the fibroblast growth factor (FGF) family of growth factors, more preferably the growth factor is FGF2, and a cytokine is administered to the dissociated neural cells, preferably the cytokine is LIF or B27.

In yet another broad aspect, the present invention provides a method for analyzing the role of genes in the regulation of neural fate specification through analysis of genetic changes which occur during the neural differentiation of the methods and cells of the present invention. In one embodiment this can be done by detecting the presence or absence of gene expression through convention techniques such as RT-PCR or methods of protein expression analysis.

In another embodiment, the invention the novel cells and methods for forming them of the invention can be used in an assay for designing and/or screening for modulators or differentiation factors of cell differentiation, preferably neural cell differentiation and development. Thus the cells and methods of the invention can be used in drug screening and discovery assays, and in tissue engineering. Such methods could involve the culturing of ES cells in serum free media, under low density conditions in the presence of such modulators or differentiation factors and in the presence or absence of cytokines, such as LIF and/or growth factors such as FGF-2. The effect on differentiation of the ES cells can then be monitored. In another embodiment, the novel primitive neural cells of the invention can be cultured in the presence of the modulator or differentiating factor and in the presence of absence of growth factors such as FGF2. The effect on differentiation can then be monitored.

Once the modulators or differentiating factors are determined, for instance the differentiation factor to develop a particular cell type from the primitive neural cell type, such cells can be used to specifically generate such cells.

In another embodiment, novel cells of the invention and cells produced by the methods of the invention can be used for therapeutic purposes, such as in transplantation or insertion of such cells to a person in need thereof. They would provide a good cell base for such activities, especially due to the ease in which they can be generated and proliferated and their homogenity.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE FIGURES

The invention will now be described in relation to the drawings in which.

FIGS. 7A and B depict cells which do not express nestin (arrow in A and B) that resemble typical undifferentiated ES cell colonies. These aggregated cells express the undifferentiated ES cell-specific marker SSEA-1 (arrowheads in C and D). Moreover, the relatively large cells that resemble nestin positive cells do not express SSEA-1 (arrow in C and D).

DETAILED DESCRIPTION OF THE INVENTION

Figure 1:
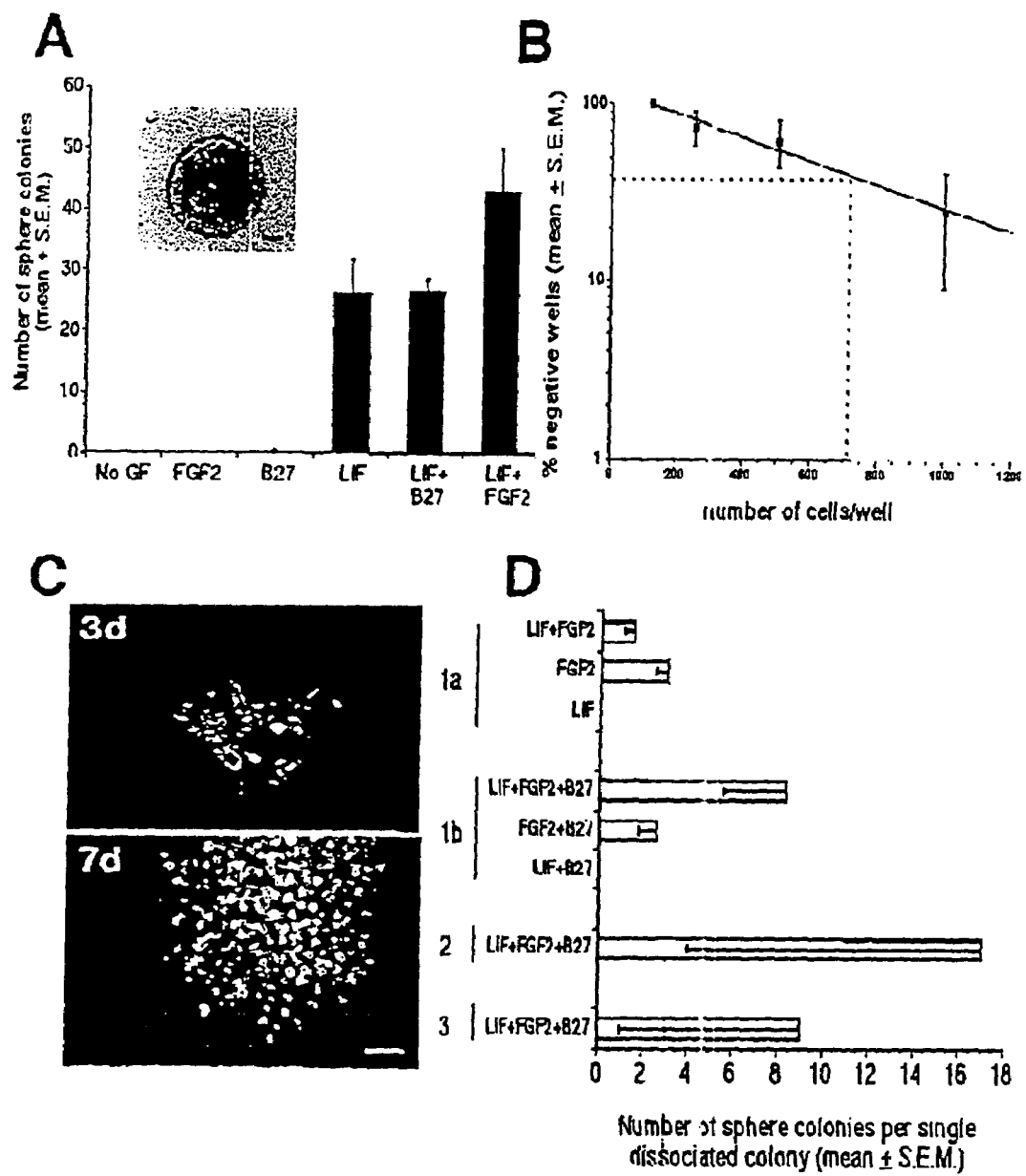
FIG. 1A is a graph showing the neural sphere colony forming ability of embryonic stem (ES) cells cultured at 20 cells/ul in chemically defined serum free media in the presence of various cytokines and growth factors and combinations thereof. The inset shows a light microscope photograph of an ES cell derived neural colony after 7 days in culture.
FIG. 1B is a graph showing limiting dilution analysis of the frequency of neural sphere colony formation from ES cells in the presence of LIF.
FIG. 1C shows inverted fluorecence microscope photographs of differentiated ES-cell derived sphere colonies, immunocytochemically labelled for the neural precursor marker nestin after 3 or 7 days in vitro.
FIG. 1D is a graph showing the secondary, tertiary and quaternary neural stem cell colony forming ability of cells dissociated from primary neural colonies and cultured in the presence of exogenous LIF, FGF2 and B27.

As mentioned above the present inventors have invented a novel primitive neural stem cell and associated methods for differentiating embryonic stem cells toward neural cells under completely defined media conditions, and methods of use of the new stem cell and methods of differentiation. As the novel primitive neural stem cell is pluripotent, it can potentially differentiate into cell types other than neural cells.

The present invention arose in part from an investigation into whether a default mechanism of neural specification could regulate the acquisition of mammalian neural stem cell identity directly from totipotent vertebrate cells.

Experiments were conducted to determine whether a default-like mechanism underlies neural specification in uncommitted mammalian embryonic stem (ES) cells.

In a preferred embodiment, the results indicate that chemically defined serum-free, feeder layer-free, low-density culture conditions are sufficient for neural differentiation of ES cells. That a novel colony-forming primitive neural stem cell population was identified displaying properties that are intermediate to ES cells and forebrain neural stem cells. Furthermore, the results indicate that the transition from ES cell to primitive neural stem cell can be enhanced by the inhibition of TGF-β-related signaling, in a manner that is consistent with a default model of neural fate specification.

ES Cells

As used in the present specification, "pluripotent ES cells" and "ES cells" are those which retain the developmental potential to differentiate into all somatic and germ cell lineages. ES cells may be derived from the inner cell mass (ICM) of the pre-implantation mammalian embryo and may be sustained in an undifferentiated state in vitro while maintaining ICM characteristics.

EB as used herein refers to embryoid body. The cells in an embryoid body are not homogenous and are difficult to propagate.

Neurospheres refers to multicellular bodies with neural markers. They can be a source of a fairly homogenous group of cells. Most cells in a neurosphere are progenitor cells in one embodiment, they comprise less than 1% of original stem cells. Cells of a neurosphere can be used to develop new spheres that comprise cells that are usually further down the differentiation pathway. Again they also comprise copies of cells from the original neurosphere. As such cells from neurospheres can be propagated.

Culture Media

As will be appreciated by those skilled in the art, "culturing the ES cells", means culturing the cells under conditions which allow for the survival of the cells for a length of time sufficient to allow for experimentation and further use of the cells. The culturing of the cells at low density in the serum-free media, includes the understanding that the conditions under which the cells are cultured are appropriate for the continued survival of the cells for the purposes for which the cells are being used.

Standard culture media typically contains a variety of essential components required for cell viability, including inorganic salts, carbohydrates, hormones, essential amino acids, vitamins, and the like. In one embodiment, DMEM or F-12 is the standard culture medium, most preferably a 50/50 mixture of DMEM and F-12. It is advantageous to provide additional glutamine, preferably at about 2 mM. Preferably, the conditions for culturing should be as close to physiological as possible. The pH of the culture medium is typically between 6–8, preferably about 7, most preferably about 7.4. In respect of pH, the term "about" means the pH mentioned plus or minus 0.5 pH units.

Cells are typically cultured between about 30–40° C., preferably between about 32–38° C., most preferably between about 35–37° C. In respect of temperature, the term "about" means the temperature mentioned plus or minus 5 degrees celcius.

Cells are preferably grown in about 5% $CO_2$. In respect of percentages, the term "about" means the percentage mentioned plus or minus 0.5 percent.

Serum-free media refers to a defined media comprising effective amounts of the following components: (a) a standard culture medium without serum, known as a "defined" culture medium, such as Dulbecco's modified Eagle's medium (DMEM), F-12, or a mixture thereof (As will be readily appreciated by those skilled in the art other defined standard media such as, for examples, Iscove's Modified Dulbecco's Medium (IMDM), RPMI, Fischer's, Alpha Medium, Leibovitz's, L-15, Noto, F 10, MEM And McCoy's may be used); (b) a suitable carbohydrate source, such as glucose; (c) a buffer such as MOPS, HEPES or Tris, preferably HEPES with glutamine and sodium bicarbonate, and (d) a source of hormones and salt including insulin, transferrin, progesterone, putrescine and selenium.

Cytokines

According to the present invention serum-free media may also be supplemented with one or more cytokines, and one or more growth factors that stimulate proliferation of cells. Cytokines comprise a diverse group of small proteins that mediate cell signaling/communication. They exert their biological functions through specific receptors expressed on the surface of target cells, and include but are not necessarily limited to leukemia inhibitory factor (LIF), ciliary neurotrophic factor (CNTF), growth hormone (GH), erythropoietin (FPO), granulocyte/macrophage colony-stimulating factor (GM-CSF), granulocyte colony-stimulating factor (G-CSF), oncostatin-M (OSM), prolactin (PRI), interleukin (IL)-2, IL-3, IL-4, IL-5-IL-6, IL-7, IL-9, IL-10, and IL-12. Interferons (IFN)-alpha, -beta and -gamma, tumor necrosis factor (TNF)-alpha, nerve growth factor (NGF), platelet factor (PF)4, platelet basic protein (PBP) and macrophage inflammatory protein (MIP)1-alpha and -beta, among others.

Growth Factors

The term "fibroblast growth factor" of "FGF" includes any protein or polypeptide having FGF biological activity, such as binding to FGF receptors, which activity has been used to characterize various FGFs, including, but not limited to acidic FGF, basic FGF, FGF2, Int-2, hst/K-FGF, FGF-5, FGF-6 and KGF.

ES Cell Differentiation

ES cell differentiation assays typically involve the formation of embryoid bodies (EB) (Martin et al., 1977; Coucouvanis and Martin, 1995) that are generated from the aggregation of numerous ES cells in the presence of serum and in the absence of LIF, a factor which normally prevents differentiation. EB resemble early embryos; in the interior, EB contain ectodermal and mesodermal tissue surrounding a cystic cavity, while externally, EB are encapsulated by primitive endoderm (Coucouvanis and Martin, 1995; 1999). Given that EB formation in very high-density cultures (25–75 times greater than the densities used in the present study) contains many different cell types (derived from all three germ layers) and are generated in the presence of 10–20% serum (which contains undefined factors), EB formation precludes a more direct analysis of the mechanisms regulating the differentiation of a specific cell lineage. Indeed, consideration of cell density and culture media parameters in studies using dissociated *Xenopus ectodermal* cells (discussed above) initiated a significant change in the understanding of vertebrate neural patterning.

The derivation of neural cells (among other cell types) from EB derived cells in vitro has been previously documented (Doetschman et al., 1985). Several studies have shown that the differentiation of neurons and glial precursors from EB derived cells can be enriched in the presence of retinoic acid (Bain et al., 1995; Fraichad et al., 1995; Strubing et al., 1995), FGF2 (Okabe et al., 1996), or PDGF (Brustle et al., 1999). Also, BMP4 has been shown to suppress neuronal differentiation of EB derived cells (Finley et al., 1999). Although these observations clearly demonstrate the potency of such factors to promote or attenuate neuronal differentiation of ES cells, each experiment was preceded by EB formation in the presence of serum. Here it is present an alternative and specific paradigm for neural cell fate specification directly from ES cells. Neural colonies can develop from ES cells in serum-free conditions in the absence of EB formation, and many single ES cells can adopt a neural (nestin+) or neuronal (βIII-tubulin+) phenotype in the absence of exogenous growth factors. The derivation of neural cells from ES cells is preferably carried out at relatively low cell densities in serum-free media. Low cell density as used herein refers to a cell culture density at which cell proliferation can occur with minimal and preferably no aggregation of ES cells or EB formation. Such densities are preferably about 50 or fewer cell/µl, most preferably less than 20 cells/µl, and even more preferred 10 or fewer cells/µl. It has been shown and a person skilled in the art would understand that the invention requires at least 1 cell to work, as such a cell density of greater than 0 is required. The present inventors have found (data not shown) that methods of the invention work significantly better in conditions where at about 10 or fewer cells/µl. Such a density results in a more homogenous cell culture i.e., primitive neural and neural cells as the case may be. The inventors have found that at this cell density, early mesodermal markers Flk1 and brachyury are not expressed in the neurospheres derived clonally at lower densities from the novel single primitive neural stem cells of the invention. At higher densities, there is a greater likelihood that some, but not necessarily all that form by aggregation of ES cells that then differentiate to multiple tissue lineages and express the early mesodermal markers as noted above.

The experiments conducted by the inventors (data not shown) showed that single ES cells at such low densities will become neural stem cells. This is known because the single cells clonally proliferated to form spheres of 10,000 to 15,000 cells, all of which stained for an early ectodermal marker (nestin) and which do not express markers of other types of tissue like mesoderm, such as flk and brachyury. When a single sphere, clonally derived from a single primitive neural stem cell (the novel cell of the invention that comes from the neural differentiation of a single undifferentiated ES cell), is dissociated the small number of neural stem cells in the sphere (that come from the symmetrical division of the original primitive neural stem cell) will proliferate to form secondary neurospheres (thus demonstrating self-renewal) that again all stain for the early neural marker nestin. In additional data (not shown), these new cells were determined not to be a tissue culture artifact but actually detectable in embryonic day 6 and 7 epiblast in the mouse. These cells can be isolated by their ability to form neurospheres in the in the presence of LIF (and not FGF2). At embryonic day 8 in the mouse, FGF2 dependent neural stem cell can be isolated from the developing neural plate.

The novel primitive neural stem cells of the invention (the LIF dependent cells) have a much greater degree of pluripotential fates than do the definitive neural stem cells isolated in similar in vitro neurosphere assays from embryonic or adult brain.

Other Uses of the Cells and of the Method of the Invention

The methods and novel primitive neural cell of the invention have many different application, especially in the field of tissue engineering, transplantation therapy an drug discovery.

In one embodiment, this paradigm may be useful in analyzing the role of single genes in the regulation of neural fate specification. For instance, the utilization of an expression-based gene trap library of ES cell lines (Stanford et al., 1998) offers a unique opportunity to employ a strategy for isolating genes that positively and negatively regulate the transition from an ES cell to a neural cell (Seaberg et al., 1999). Thus, the present findings underscore the potential for using ES cell models of mammalian neural development.

The present methods and novel cell line of the invention can be used to screen potential modulators of cellular differentiation, preferably neural differentiation, but not necessarily so. As the primitive neural cells of the invention are plutipotent and can differentiate into cell types other than neural cell types under suitable conditions. The term "modulators" as used herein refers to any module or factor (such as pH, Temperature, Time, isotonic conditions, etc) that can potentially effect cellular differentiation.

In one assay for screening modulators of cellular differentiation the pluripotent ES cells can be cultured under serum free, low density conditions in the presence or absence of LIF, in the present of the modulator, and in the present or absence of TGF2, as the situation requires, and the effect on differentiation can be detected.

One can also use the methods and cells of the invention to study conditions associated with cellular development and screen for potential therapeutic or corrective drugs or modulators of the condition. This can be carried out in one embodiment by comparing the development of normal ES cells with cells from those having the condition.

The present inventors have identified the primitive neural stem cells in vivo, as such it is suitable for simulating an in vivo model. In one embodiment the novel primitive stem cell is LIF dependent. In another embodiment it is pluripotent. Such cells can be used in assays for drug discovery, screening for drugs and differentiation (modulating) factors, etc. They can also be used as a good source of a relatively homogenous cell base. They can be used themselves in the treatment, or therapy of certain conditions such as in transplantation therapies, especially for conditions of neurological system, resulting in neural cell damage or loss (paralysis (regeneration of neural connections), parkinson's disease, alzheimers, multiple sclerosis). Due their pluripotency, they can also be used in developing tissues, neural or otherwise. Such tissues could be used in transplantation therapy for conditions other than those related to the neural system. For instance, the cells of the invention could be used to develop insulin producing cells for the treatment of diabetes. The cells could also be used to develop a desired cell type by propagating them under predetermined conditions conducive to development of such cell type. The cells can also be used to determine what these conditions may be. Various conditions for ES cell differentiation into multiple cell types can be found in J. Yamashita et al Nature 408 page 92.

In studying modulators of cellular differentiation, the novel cells of the invention can be cultured in the absence or presence of FGF-2 and the potential modulator, to determine the effect of the modulator on neural cell development.

The following non-limiting examples are further illustrations of the invention of the present specification.

EXAMPLES

GENERAL MATERIALS AND METHODS FOR THE EXAMPLES

Propagation and maintenance of ES cells

The ES cell line R1 was grown on mitotically inactive fibroblast feeder layers maintained in DMEM+10% FCS culture medium containing LIF (1000 U/ml) at low passage number (6–11) as previously described (Nagy and Rossant, 1993). For passaging ES cells, cultures were disaggregated with 0.05% trypsin dissolved in Tris-saline/EDTA for 5–10 minutes, mechanically dissociated, centrifuged and resuspended in culture medium.

Culturing ES cells

Passaged ES cells were washed (2 times), centrifuged and resuspended in chemically defined serum-free media (Reynolds et al., 1992; Reynolds & Weiss, 1996) composed of a 1:1 mixture of Dulbecco's modified Eagle's medium (DMEM GIBCO) and F-12 nutrient (GIBCO) including 0.6% glucose (Sigma), 2 mM glutamine (GIBCO), 3 mM sodium bicarbonate (Sigma), and 5 mM HEPFS buffer (Sigma). A defined hormone and salt mixture (Sigma) that included insulin (25 (g/ml), transferrin (100 (g/ml), progestrone (20 nM), putrescine (60 (M), and selenium chloride (30 nM) was used instead of serum. ES cells were plated at various cell densities in 24-well culture plates (Nunclon) in the presence of either LIF (1000 U/ml), LIF+ FGF2 (10 ng/ml; Upstate Biotech or Sigma) and 2 (g/ml heparin (Sigma), or in the absence of any exogenous growth factors. For short term (4–24 hours) neural differentiation, ES cells were plated in identical culture conditions in 24-well culture plates (Nunclon) that were precoated with poly-L-ornithine (15 µg/ml, Gibco).

Limiting dilution analysis was performed as previously described (Bellows and Aubin, 1989; Tropepe et al., 1999). ES cells were plated in 24-well plates containing LIF (1000 U/ml). Cell numbers were adjusted to give a starting concentration of 5000 cells/ml from which serial dilutions were made. Final cell dilutions ranged from 1000 cells per well to 1 cell per well in 0.5 ml aliquots. Cultures were left undisturbed for 7 days after which time the fraction of wells not containing sphere colonies for each cell plating density was calculated and those points were plotted against the number of cells plated per well. The number of cells required to form one sphere colony, which reflected the proportion of neural stem cells in the entire population, was then determined from the point at which the regression line crossed the 0.37 level (37%). That is $F_0=e^x$, where $F_0$ is the fraction of wells without sphere colonies and x is the mean number of cells per well. Based on a Poisson distribution of cells, $F_0=0.37$ corresponds to the dilution at which there is one neural stem cell per well. The linear relationship observed between the cell density and the number of sphere colonies generated (regression coefficient $R^2=0.99$) can be accounted for by the clonal proliferation of a single rare population of cells.

To assess colony formation at clonal densities, ES cells were plated in serum-free media containing LIF (as above) at $5 \times 10^4$ cells per 94 mm Greiner hybridoma tissue culture dish (Fedoroff et al., 1977). which is subdivided into approximately 700 microwells, 0.04 $cm^2$ each (Creiner Labortechnik, Bellco Glass, Ind., Vineland, N.J.). Using this procedure, microwells contained ~15 viable cells per well (randomly assorted). Cultures were maintained for a 7-day period.

Self-renewal of primary colony-formin) ES cells was assessed as previously described (Tropepe et al., 1999). Single sphere colonies were isolated, mechanically dissociated into a single cell suspension in 0.2 ml of serum-free media containing various combinations of LIF (1000 U/ml), EGF2 (10 ng/ml), heparin (2 (g/ml), EGF (20 ng/ml; Upstate Biotech) or B27 supplement (1X) and cultured in 96-well (Nunclon) plates. Secondary sphere colonies were quantified after 7–10 days. A similar procedure was used for repeated passaging experiments. Cell viability after a 7-day culture period (sphere colony assay) or after 4–24 hours (short-term ES differentiation assay) was determined using trypan blue exclusion (1:2 dilution of 0.4% trypan blue; Gibco).

To determine the effect of a targeted null mutation in the Smad4 gene on neural colony formation, clones C8–13 (–/–), C8–24 (/), F9–2 (–/–), F0–5 (–/–) and the wildtype E14K (+/+) ES cell lines (Sirard et al., 1998) were used. There were no differences in colony formation between the various (–/–) ES cell clones and thus the analysis included the pooled results from all of the clones. Human recombinant BMP4 protein (stock 0.812 mg/ml) was provided by Genetics Institute Inc. and human recombinant Noggin protein (stock 1.05 mg/ml) was provided by Regeneron Pharmaceuticals Inc.

Embryonic and adult dissections

Adult or Pregnant CD1 mice (Charles River, Quebec) of gestational age 9.5 (E9.5) or E14.5 (see below) dissected as previously described (Chiasson et al., 1999; Iropepe et al. 1999). In order to assess positive immunolabeling, E14.5 dissections of embryonic brain and skin were prepared as above and plated on a MATRIGEL substrate at high cell densities (~100cells/ml) in the same culture media containing 1% FBS. For RT-PCR analyses, tissues (e.g. brain, somite, liver, footpad epidermis) that served as positive controls were dissected and enzymatically treated in a similar fashion prior to RNA extraction.

Embryonic and adult forebrain dissections

Pregnant CD1 mice (Charles River, Quebec) of gestational age (9.5 (E9.5) or E11.5 (see below) were killed via cervical dislocation and embryos were removed as previously described (Chiasson et al., 1999; Tropepe et al., 1999). Dissected germinal zone from the E9.5 telencephalon was transferred to serum-free media and mechanically dissociated into a cell suspension with a fire-polished Pasteur pipette. Cell viability was assessed using trypan blue. Cells were plated at 10 cells/µl in 24-well (0.5 ml/well) uncoated plates (Nunclon) in serum-free media containing either FGF2 (10 ng/ml)+heparin (2 (g/ml) or FGF2+heparin+LIF (1000 U/ml). Self-renewal of neural stem cells that generated primary sphere colonies (selecting mainly floating colonies after 7 days in vitro) were routinely subcloned by mechanically dissociating a single colony in 0.2 ml of serum-free media, in identical growth factor conditions as the primary culture, and plated in uncoated 96-well (0.2 ml/well) plates (Nunclon). The number of new secondary colonies was quantified after a further 6–7 days in vitro. Neural stem cell colonies from the adult forebrain subependyma were isolated as previously described (Chiasson et al., 1999) and cultured as above.

Immunocytochemistry

Single sphere colonies were transferred to a well coated with MATRIGEL basement membrane matrix (15.1 mg/ml stock solution diluted 1.25 in serum-free media; Becton-Dickinson) in individual wells of a 24-well culture plate (Nunclon) (0.5 ml/well). Immunochemistry was performed as previously described (Tropepe et al., 1999). For nestin immunolabeling, sphere colonies were allowed to adhere for 24 hours in serum-free media prior to fixation. Adherent colonies were fixed with 4% paraformadlehyde in PBS (pH 7.2) for 20 min at room temperature and then washed (3x) with PBS (5 min each). Colonies were then permeabilized with 0.3% Triton X-100 for 5 min, washed (2x) with PBS (5 min each) and then incubated for 1 hour in 10% normal goat serum (NGS) at room temperature in order to presaturate non specific protein binding sites. A rabbit polyclonal antiserum (a gift from Dr. R. McKay) (Tohyama et al., 1992) was diluted to 1:1000 (in PBS+10% NGS) and colonies were incubated overnight at 4° C. The next day, sphere colonies were washed (3x) in PBS (5 min each) and subsequently incubated with a secondary goat anti-rabbit FITC-conjugated antibody (1:200; Sigma) for 30 min at 37° C.

After rinsing three times (5 minutes each), all cultures were incubated in Hoechst 33258 nuclear stain (0.015 mg/ml stock solution diluted to 0.001 mg/ml; Boehringer Mannheim) for 5 minutes at room temperature in order to facilitate cell quantification. After washing (3×) (5 min each), colonies were coated with Fluor-mount mounting medium. Fluorescence was detected on a Nikon inverted fluorescence microscope. A similar procedure was used for longer-term differentiation of sphere colony cells. After 7 days in culture, colonies that were spread out on the substrate were fixed in 4% paraformaldehyde (in PBS, µH 7.2) for 20 minutes at room temperature followed by 3 (5 minutes each) washes in FBS (pH 7.2). Cells were then permeabilized for 5 minutes in PBS containing 0.3% Triton X, rinsed for 5 min (2×) in PBS and blocked for 1 hour in PBS containing 10% normal goat serum (NGS). After blocking, cultures were incubated in anti-MPA-2 mouse monoclonal (IgG) (1:1000; Boehringer Mannheim) and anti-GFAP rabbit polyclonal (IgG) (1:400: Chemicon) antibodies diluted in PBS containing 10% NGS overnight at 4°. Cultures were then rinsed in PBS three times (5 minutes each) and subsequently incubated in FITC goat anti-rabbit (1:200 Jackson ImmunoResearch) and TRITC goat anti-mouse (1:200; Jackson ImmunoResearch) secondary antibodies at 37° C. for 30 min. Cultures were rinsed three times (5 minutes each) in PBS. Separate cultures (from similar conditions) were used for oligodendrocyte immunolabeling. Cultures were incubated in anti-O4 mouse monoclonal (IgM) antibody (1:40; Boehringer Mannheim) in PBS containing 10% NGS at 4° C. overnight. The next day, cultures were rinsed three times (5 minutes each) and subsequently incubated in DTAF goat anti-mouse-IgM (1:200; Jackson ImmunoResearch) secondary antibody in PBS containing 10% NGS at 37° C. for 30 minutes. After rinsing three times (5 minutes each), all cultures were incubated in Hoechat 33258 nuclear stain (0.015 mg/ml stock solution diluted to 0.001 g/ml; Boehringer Mannheim) for 5 minutes at room temperature in order to facilitate cell quantification. Colonies were washed (3×) in PBS (5 min each) and then coated with Fluormount and fluorescence was visualized using a Nikon Inverted-fluorescence microscope. Secondary antibody-only control cultures were processed simultaneously using the identical protocol except dilution solutions were devoid of primary antibodies. All secondary controls were negative for immunolabeling.

For short-term (24 hours) differentiation experiments, ES cells were adhered to a poly-L-ornithine substrate (15 µg/ml; Sigma), fixed in 4% paraformaldehyde (as above) and immunolabeled using primary mouse monoclonal anti-βIII-tubulin antibody (1:000; Sigma), anti-nestin antibody (as above) and rabbit anti-mouse Oct-4 antibody (1:400; a gift from Dr. J. Cross). Cultures were counter-labeled with Hoechst (as above) and quantifed by counting 3–4 random standardized areas (using an ocular grid) at 20X objective magnification per culture.

To cryosection ES derived or forebrain derived sphere colonies, colonies were rinsed (2×) by transferring to PBS (pH 7.2) for a few seconds with a Pasteur pipette. Colonies were then transferred to 4% paraformaldehyde containing 0.4% pleric acid in 0.16 M phosphate-buffer (pH 6.9) and fixed for 1 hour at room temperature. Sphere colonies were then rinsed (3×) in 10 mM PBS for 5 min each prior to being resuspended in 10% sucrose (in 10 mM PBS) overnight at 4° C. The following day, sphere colonies were placed in tissue freezing media (Tissue Tek) in order to quick freeze to −50° C. Using a cryostate, 14 µm sections were taken and collected on gelatin coated slides. Slides were stored at −70° C. and subsequently processed for nestin or nuclear Oct4 immunolabeling (as above).

RT-PCR analysis

Total RNA was isolated using the RNeasy extraction kit (Qiagen) and 1 µg of total RNA was used to synthesize cDNA with oligo-d(T)$_{12-18}$ primers and MuMLV reverse transcriptase (Superscript II; Boehringer-Mannheim) at 42° C. for 1 hour. The PCR mixture (20 µl) consisted of 1 µl cDNA, 16 pmol 5'' primer, 16 pmol 3' primer, specific for the gene in question 0.2 mM dNTP, 2 µl PCR reaction buffer and 0.8 U of Taq polymerase (Promega). cDNA was amplified in a thermal cycler (Perkin-Elmer) For all primer pairs denaturation for 30 sec at 94° C., annealing for 30 sec and extension at 72° C. was used. The sense and antisense primers, Mg$^2$ concentration, annealing temperature, extension time and number of PCR cycles were used for the following genes. Emx2: sense 5'-CTCCCAGCTTT-TAACGCTAGA-3' (SEQ ID. No. 1), antisense 5' CTTTTGCCTTTTGAATTTCGTTC-3'(SEQ. ID. No. 2), 1.65 mM Mg$^{2+}$, 56° C., 40 sec, 40 cycles. HoxB1: sense 5'-CCGGACCTTCGACTGGATG-3'(SEQ. ID. No. 3). antisense 5'-GGTCAGAGGCATCTCCAGC-3'(SEQ. ID. No. 4), 1.35 mM Mg$^{2+}$, 58° C., 40 sec, 40 cycles. Otx1: sense 5'-TCACAGCTGGACGTGCTCGA-3'(SEQ. ID. No. 5). antisense 5'-GCGGCGGTTCTTGAACCAAA-3'(SEQ. ID. No. 6), 1.65 mM Mg$^{2+}$, 58° C., 40 sec, 40 cycles. Six3: sense 5'-CGCGACCTGTACCACATCCT-3'(SEQ. ID. No. 7), antisense 5'-GCCTTGGCTATCATACGTCA-3'(SEQ. ID. No. 8), 1.35 mM Mg$^{2+}$, 56° C., 40 sec, 40 cycles. Brechyury: sense 5'-AGTATGAACCTCGGATTCAC-3'(SEQ. ID. No. 9), antisense 5'-CCGGTTGTTACAAGTCTCAG-3'(SEQ. ID. No. 10), 1.65 mM Mg$^{2+}$, 56° C., 1 min. 35 cycles. G ATA4: sense 5'-AGCCTACATGGCCGACGTGG-3'(SEQ. ID. No. 11) antisense 5'-TCAGCCAGGACCAGGCTGTT-3'(SEQ. ID. No. 12), 1.35 mM Mg$^{2+}$, 58° C., 1 min, 35 cycles. H NF-4: sense 5'-CCATGGTGTTAAAG-GACGTGC-3'(SEQ. ID. No. 13), antisense 5'-TAGGAT-TCAGATCCCGAGCC-3',(SEQ. ID. No. 14) 1.35 mM Mg$^{2+}$, 56° C., 1 min, 35 cycles. CK-17, sense (SEQ. ID. No.), antisense (SEQ. ID. No.) As a control, cDNA amplification of the GAPD gene (glyceraldehyde-3-phosphate dehydrogenase) was simultaneously run in each PCR experiment. Primers for CAPDH: sense 5'-ACCACAGTCCAT-GCCATCAC-3'(SEQ. ID. No. 15), antisense 5'-TCCAC-CACCCTGTTGCTGTA-3'(SEQ. ID. No. 16) and PCR reaction conditions were similar to conditions used for Emx1 amplification (see above) Amplified products were electrophoresed in 2% agarose gel containing ethidium bromide (25 µg/ml) and bands were visualized with UV light (Duallite Transilluminator, Fisher Biotech).

Expression of mouse *Cerberus*-like in Neuro2a cells

Neuro2a (a murine neuroblastoma cell line) cells were seeded at 1×10$^6$ cells per 100 mm petri dish and transiently transfected with 10 µg of plasmid DNA by means of LipofectAMINE (Gibco) according to the manufacturer's instructions. After 6 hours, the culture media was changed to 10 ml of DMEM+10% FBS (Gibco). Twenty-four hours after transfection, culture media was changed to 0 ml of serum-free media. Seventy-two hours after transfection, cell supernatant was collected and centrifuged to remove cellular debris. Supernatant media was aliquoted and stored at −70° C. Addition of 4% (v/v) of supernatant (3 separate experiments) resulted in a similar increase in colony formation compared to the addition of 20% (v/v) supernatant (2 separate experiments), but this effect was considerably variable from one experiment to the next, whereas addition of 20% (v/v) supernatant resulted in a very consistent increase between experiments. Thus data from the 20% (v/v) experiments were used for the analysis. The plasmids pCS-V2 (gift from Dr. R. Moon) Hoppler et al., 1996) and pCS-cer-I (a gift from Dr. E. De Robertis) (Belo et al., 1997) were used.

Generation of chimeras

ES sphere colonies were generated using ES cells harboring a yellow-fluorescent protein (YFP) transgene or cyan-fluorescent protein (CFP) transgene (gifts from Drs K. Hadjatonakis and A. Nagy). Embryonic or adult telencephalon-derived sphere colonies were generated from either green fluorescent protein (GFP) transgenic mice (a gift from Drs. K. Hadjantonakis and A. Nagy) or ROSA mice ubiquitously expressing the LacZ gene product β galactosidase (β-gal) (Jackson Laboratory) (Friedrich and Soriano, 1991). ES-derived, E9.5, E14.5 or adult telencephalon derived sphere colonies were aggregated with diploid CD1 morulastage embryos for 24 hours in vitro as previously described (Nagy and Rossant, 1993). Once integrated, the colony-embryo aggregates were then transferred into pseudo-pregnant CD1 females, harvested at embryonic day E8.5–E9.5 and either stained for β-gal activity (for ROSA-CD1 chimeras) or visualized for fluorescence (GFP-CD1 chimeras). β-gal activity was detected by rinsing embroyos in a 100 mM sodium phosphate buffer (pH 7.3), fixing in 0.2% gluteraldehyde, 2 mM $MgCl_2$, 5 mM EGTA and 100 mM sodium phosphate (pH 7.3) at room temperature for ~15 min. Embryos were then rinsed (3×) in a wash buffer containing 0.02% NP-40, 0.01% deoxycholate, 2 mM $MgCl_2$, and 100 mM sodium phosphate (pH 7.3) for ~10 min each. Embryos were stained in 1 mg/ml X-gal, 5 mM $K_3Fe(CN)_5$, 5 mM $K_4Fe(CN)_6$, 0.02% NP-40, 0.01% deoxycholate, 2 mM $MgCl_2$, and 100 mM sodium phosphate buffer (pH 7.3) at 37° C. overnight.

EXAMPLE 1

Single ES cells differentiate into colony forming neural stem cells in the absence of serum, feeder layers or the formation of EB To determine directly the capacity for ES cells to adopt a neural fate in the absence of serum-derived or feeder layer-derived factors and in the absence of cell-cell contact found in embryoid bodies, ES cells were cultured at relatively low cell densities in a chemically-defined, serum-free media. Under similar conditions, single neural stem cells isolated from the embryonic germinal zone of the neural tube can proliferate in response to exogenous EGF or FGF2 to give rise to clonal colonies of undifferentiated neural precursor cells that form floating spheres (Reynolds et al., 1992; Tropepe et al., 1999). The colony-forming neural stem cells have the classical stem cell properties of self-renewal and multipotentiality (Potten and Loeffler, 1990; Morrison et al., 1997). That is, a small percentage of cells isolated from single dissociated colonies can generate new clonal colonies (self-renewal), while the majority of cells within the colonies will differentiate into either neurons and glia, astrocytes or oligodendrocytes, (Reynolds and Weiss, 1996).

When ES cells were cultured at relatively low cell densities in the presence of either EGF or FGF2 or in the absence of oxogenous growth factors, no cell colonies were generated (FIG. 1A). In contrast, in the presence of exogenous leukemia inhibitory factor (LIF), which is normally used to maintain ES cells in an undifferentiated state (Smith et al, 1988; Williams et al., 1988), floating sphere-like colonies were generated after 7 days in vitro. There was no significant difference in the numbers of neural stem cell colonies generated when either EGH or FGF2 were combined with LIF compared to LIF alone, although the presence of FGF2 produced a non-significant trend toward facilitating LIF-dependent colony formation (FIG. 1A). Thus, exogenous EGF and FGF2 were neither necessary nor sufficient for colony formation in primary cell cultures. Furthermore, CNTT, another member of the cytokine family of signaling molecules to which LIF belongs (Kishimoto et al., 1994), was unable to substitute as a colony-promoting factor (data not shown), suggesting that the effects of LIF are specific.

To determine the frequency of cell colony formation, ES cells were cultured at various cell densities (from 1 cell/well to 20 cells/μl) in 24-well culture dishes in a limiting dilution assay (Bellows and Aubin, 1989; Tropepe et al., 1999). The estimated frequency of sphere colony forming cells in the presence of LIF was ~0.2% (FIG. 1B). No sphere colonies were observed at cell densities of less than 500 cells per well (0.5 ml of media), suggesting that a threshold number of cells may be required in order to facilitate the clonal proliferation of a single ES cell However, it was found that the present invention would work with even a single cell. To show this, ES cells were cultured at ~15 cells per microwell randomly distributed in Greiner hybridoma culture dishes subdivided into 700 microwells (0.04 $cm^2$ each). Even though the majority of microwells contained cells, an average of 35 colonies were generated (2 separate cultures) over the entire dish. Hence, a similar frequency of sphere colony formation was observed over the entire culture dish (i.e. 15×700–10,500 cells, an average of 35 colonies (10,500=0.3%). Furthermore, in one additional experiment, single ES cells were cultured in 96-well plates (0.2 ml) and 1 sphere colony was generated in 600–700 wells scored. Thus, the results demonstrate that a very small percentage of single ES cells generate sphere colonies under these conditions as predicted by the limiting dilution analysis.

EXAMPLE 2

Colony-forming ES cells show neural stem cell characteristics

Sphere colonies generated in the presence of LIF grew to a size of approximately 300–500 μm in diameter after 7 days and were composed of cells that all expressed the intermediate filament protein nestin, which is expressed in neural precursor cells in embryonic and adult CNS tissues and transiently in muscle progenitors (Lendahl et al. 1990) and in some epithelial derivatives (Mokry and Nemecek, 1998) (FIG. 1C). An analysis of smaller sized colonies identifiable at 3 days in culture (composed of 20–30 cells) demonstrated that all of the cells within these colonies (determined by counting Hoechst stained nuclei) appeared to express nestin. Thus, nestin expression is correlated with the initial formation of the sphere colony, coinciding with nestin expression in single ES cells a the onset of the cell culture period prior to sphere colony formation and no cells within the colonies retained nuclear expression of the ES cell marker Oct-4 (see below). These data suggest that individual ES cells acquire a neural precursor cell identity before they proliferate to generate neural colonies.

Individual colonies were dissociated and subcloned as previously reported (Reynolds et al., 1992; Topepe et al., 1999) in the presence of exogenous LIF, FGF2 or EGF alone, or in combinations. Regardless of the primary culture conditions the formation of secondary neural stem cell colonies was dependent upon the presence of exogenous FGF2. LIF alone was not sufficient for secondary colony formation (FIG. 1D). The colony-forming ability in tertiary and quaternary subcloned cell cultures could be sustained with combined FGF2 and LIF. However, substituting for LIF with a B27 media supplement (thought to prevent excessive cell death by inhibiting free radical-induced cellular damage) in the FGF2 cultures was sufficient for repeatedly generating new sphere colonies (FIG. 1D). Furthermore, the ability to generate sphere colonies in the presence of exogenous EGF alone, EGF+LIF or EGF+LIF+B27 was not observed and the effect of EGF+FGF2 was similar to the effects of FGF2 alone. The relatively small expansion of ES sphere colonies (2–16 now clonal colonies arise from the dissociation of a single ES derived neural colony; FIG. 1D) is similar to the primary subcloning of FGF-responsive neural stem cells isolated form the E8.5 anterior neural plate (Tropepe et al., 1999). Under conditions of the present invention, however, new ES derived colonies maintain their FGF2 and LIF (or B27) dependence upon repeated subcloning whereas the E8.5 derived neural stem cell colonies require only FGF2. Furthermore, a separate EGF-responsive population of colony-forming cells, which occurs during the development of the neural stem cell lineage between E10.5 and E14.5 in vivo (Tropepe et al., 1999; Martens et al., 2000) was not established from the ES-derived colonies.

To determine if the individual cells giving rise to the neural colonies had neural multilineage potential individual colonies were encouraged to fully differentiate (placed on a MATRIGEL substrate and in the presence of 1% FBS) for a period of 7 days. Under these conditions, each of the differentiated colonies contained neurons (MAP2$^+$ or β-III tubulin$^+$), astrocytes (CFAP$^+$) and oligodendrocytes (O4$^+$) using these conventional cellular markers of differentiation (FIG. 2A). The neural cells identified in these differentiated cultures (including undifferentiated, nestin$^+$ cells) accounted for all of the cell types present in the colonies. At least one non-neural marker, the muscle determination gene product MyoD, was no detectable by immunocytochemistry in these colonies, even though MyoD$^+$ cells were identified in control explant cultures of E9.5 somitic mesoderm (data not shown). ES cells (not from ES colonies) cultured for 7 days in the same differentiation conditions at high cell densities do not express the neuronal markers MAP2 or β-III tubulin. Thus, at relatively high all densities, ES cells must be specified to a neural identity (neural stem cell colonies) in order to differentiate into neurons and glia.

To further examine the lineage commitment of the ES-derived sphere colonies, we analyzed the expression of genes restricted to neural and non-neural lineages using RT-PCR analysis (FIG. 2B). Sphere colonies did not express the early mesoderm-specific transcription factor brachyury (Beddington et al., 1992), which is abundant in EB (Elefanty et al., 1997). Sphere colonies expressed the early endodermal marker CATA4, a zinc finger transcription factor that binds to a core GATA motif in the cis regulatory elements of many genes (Arceci et al., 1993). However, the gene HNF-4, which is a later endodermal marker (Taraviras et al., 1994; Li et al., 2000), was not expressed in ES-derived neural colonies suggesting only partial endodermal potential with the colonies, unlike full endodermal potential documented for EB differentiation. Consistent with this observation, the absence of Otx1, expressed during the formation of the anterior visceral endoderm and later in the forebrain (Acampora et al., 1998), suggest that sphere colonies do not engage in full visceral endoderm differentiation. Finally, the epidermal marker Cytokeratin-17 (McGowan and Coulombe, 1998) was not expressed in colonies.

Specific neural mRNAs were expressed in isolated ES-derived sphere colonies. The dorsal telencephalon-specific homeodomain transcription factor Emx2 (Simeone et al., 1992), and the hindbrain and spinal cord specific transcription factor HoxB1 (Wilkinson et al., 1989) were expressed in the ES-derived neural sphere colonies (FIG. 2B). However, the anterior neural gene Six3 (Oliver et al., 1995), like Otx1, was not expressed. As a control, neural colonies derived from E14.5 forebrain germinal zone were assayed for the expression of lineage-specific genes. Although neural specific gene expression was confirmed in these samples (FIG. 2B) expression of the non-neural genes brachyury, GATA4 and HNF-4 was not observed (data not shown). In addition, ES cells freshly trypsinized form their feeder-layers were also used as controls. With the exception of GATA4, Otx1 and HNF4, the unmanipulated ES cells express all of the genes tested, and indeed are known to non-specifically express a variety of genes (Elefanty et al., 1997). Interestingly, neural-specific gene expression persisted in the sphere colonies, whereas the mesodermal marker Brachury was downregulated in the transition from ES cells to neural colonies. Thus, sphere colonies generated through the proliferation of a single neural cell are specified to primarily a neural identity and are composed of both neuronal and glial lineages. The fact that some non neural genes (e.g. GATA4) are expressed in sphere colonies may suggest that these specified neural stem cell derived colonies are not completely committed to a neural fate, but may retain pluripotent or more primitive characteristics (see below) than the neural stem cells isolated from the embryonic and adult nervous system. Furthermore, the vast majority of non-colony forming ES cells adopt a neural (and even neuronal) cell fate as early as 24 hours (see below). The absence of Otx1, which is expressed in the anterior neural tube and anterior visceral endoderm, further may indicate that early anterior-posterior polarity is not intrinsic to sphere colonies.

EXAMPLE 3

LIF functions as a persmissive factor for neural stem cell differentiation of ES cells The ability of LIF to specifically promote neural colony formation in serum-free media (in the absence of oxogenous growth factors) may indicate the LIF induces uncommitted ES cells to a neural fate in primary cultures. However, there are numerous examples in the literature where the presence of LIF was necessary to maintain ES cells in an undifferentiated state (reviewed in O'Shea, 1999), while LIF withdrawal was coincident with differentiation (e.g. Doetschman et al., 1985). Two observations in the present study suggest that LIF may act in a permissive manner to enable ES cells to adopt a neural stem cell fate.

First, since neural stem cells isolated form the E8.5 neural plate are dependent upon FGF (Tropepe et al., 1999). It was tested whether endogenous FGF signaling mediates neural colony formation in primary ES cell cultures in the presence of LIF. We utilized a FGF-receptor-1-deficient (FGFR1$^{(-/-)}$ ES cell line (compared to a FGFR1$^{(+/-)}$ control cell line; Ciruna et al., 1997) and assayed for neural colony formation. In the absence of functional FGFR1 signaling, the ability of ES cells to adopt a neural stem cell fate and generate colonies after 7 days in vitro was diminished by 82% in the presence of LIF (FIG. 3A), suggesting that ES cells may be responding to endogenous FGF that is released by the ES cells. Consistent with this notion, the addition of an anti-FGF2 antibody to a primary ES cell culture in the presence of LIF caused a >95% decrease in the number of neural colonies observed after 7 days (FIG. 3B). These results demonstrate that although the addition of exogenous FGF2 is not necessary for neural colony formation in the presence of LIF, endogenous FGF signaling is required.

Second, exogenous LIF can enhance the numbers of FGF-responsive neural stem cells from the E9.5 forebrain that proliferate to form sphere colonies in the presence of FGF2, compared to cultures with FGF2 alone (FIG. 3C), but LIF alone is not sufficient for E9.5 neural stem cell proliferation. Furthermore, LIF (as well as B27) can promote the repeated subcloning of ES-sphere colonies that are FGF-dependent. These results indicate that although LIF is critical for the early transition of ES cells into colony-forming neural stem cells, it may act primarily as a permissive factor to maintain cell survival in these minimal conditions. In contrast, FGF signaling is critical at all stages of neural stem cell colony formation, but it is unclear if it is involved in the induction of the neural differentiation of ES cells or simply in promoting proliferation in our colony-forming assay.

EXAMPLE 4

Inhibition of TGFβ-related signaling enhances neural stem cell differentiation of ES cells.

Given that very few of the cultured ES cells generated sphere colonies (~0.2%), it was sought to determine if the release of endogenous BMP from the ES cells inhibited neural sphere colony formation, as would be predicted from the neural default model. To test whether BMP could inhibit ES sphere colony formation, BMP4 (5 ng/ml) was added to ES cell cultures containing LIF and FGF2. A greater than 50% decrease in the number of sphere colonies generated was observed and this effect appeared to be maximal since a 5-fold increase in BMP4 concentration did not further significantly attenuate the number of sphere colonies generated (FIG. 4A). The addition of the BMP protein antagonist Noggin (100 μg/ml) to the primary ES cell cultures caused a 50% increase in the number of sphere colonies generated (FIG. 4B). This increase appeared to be maximal since an increase in Noggin concentration from 10 μg/ml to 100 μg/ml resulted in no additional increase in the numbers of sphere colonies generated.

It is evident that although Noggin can enhance the numbers of ES cells that differentiate into neural colony-forming stem cells, the effect is moderate, it is possible that Noggin may eventually lose its activity and degrade with our extended culture periods. Alternatively, Noggin is known to be less effective than Chordin in neural induction assays in Xenopus (Lamb et al., 1993) and targeted null mutations in both Noggin and Chordin are required to demonstrate anterior neural development deficits in mice in vivo (Bachiller et al., 2000). Thus, the moderate increase in the numbers of ES cells that will differentiate into neural sphere colony-forming stem cells in the presence of exogenous Noggin may underestimate the role for BMP-mediated inhibition of neural stem cell colony formation. Certainly, BMP4 and BMP-receptor-1 are expressed by undifferentiated ES cells (Elefanty et al., 1997). To determine more directly the effect of blocking BMP signaling, we utilized an ES cell line with a targeted null mutation in the Smad4 gene (Sirard et al., 1998), an intracellular transducer of TGFβ-related signaling (Wrana, 2000). Since Smad4 is a critical common component for multiple TGFβ-related signaling pathways, we reasoned that a null mutation in the Smad4 gene would abrogate most of the BMP signaling that could potentially inhibit neural sphere colony formation. Smad4$^{(/)}$ ES cells cultured in the presence of LIF generated a 4–5 fold increase in the numbers of neural sphere colonies, compared to the wildtype E14K cell line used to generate the targeted mutation (FIG. 4C). The baseline numbers of sphere colonies generated by wildtype R1 ES cells (26.3±5.4) and wildtype E14K ES cells (25.7+67) cultured at 20 cells/μl were not significantly different (t=0.08, p>0.05). Interestingly, the rate of proliferation between wildtype and Smad4$^{(-/-)}$ cells in high or low serum concentration is similar, indicating that the increase in the number of colonies from mutant ES cells is likely not a result of a general increase in proliferation. The increase in neural colonies in Smad4$^{(-/-)}$ was greater than the augmented numbers of sphere colonies observed in the presence of exogenous Noggin, possibly because Smad4 inactivation is more effective in inhibiting BMP signaling. Taken together, these results indicate that BMP4 signaling has a specific effect in limiting the numbers of single ES cells that differentiate into colony forming neural stem cells and that inhibition of this pathway is sufficient to enhance neural stem cell colony formation. Importantly, the Smad4 $^{(-/-)}$ primary neural stem cell derived colonies did not passage at a greater rate compared to control primary neural stem cell colonies (data not shown), suggesting that the effect of the mutation is on the transition from ES cell to neural stem cell and not on the later symmetrical division of the neural stem cells.

Figure 4:
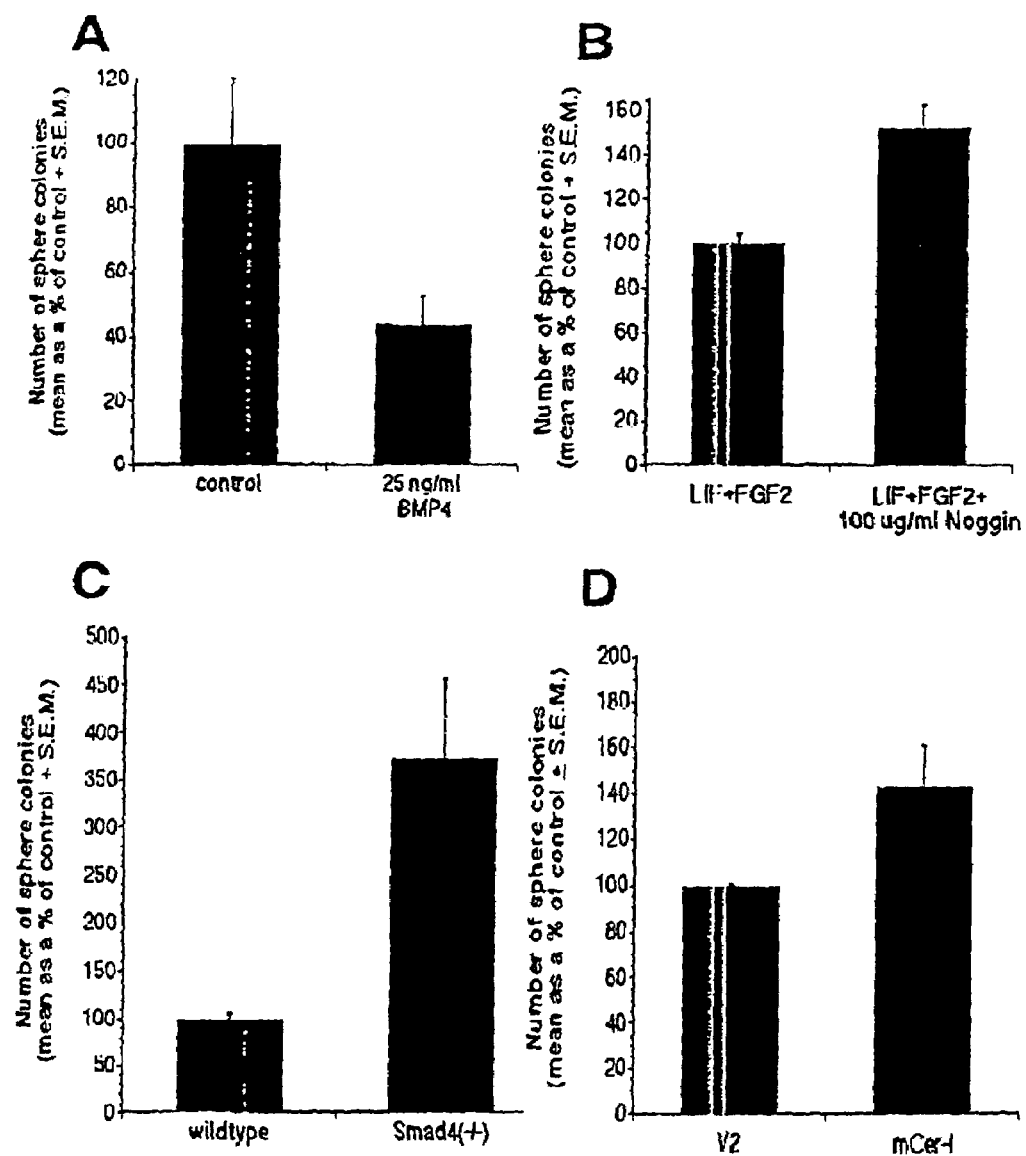
FIG. 4A is a graph showing the neural colony forming ability of ES cells cultured in the presence of LIF and FGF2 alone or in the presence of BMP4.
FIG. 4B is a graph showing the neural colony forming ability of ES cells cultured in the presence of LIF and FGF2 alone or in the presence of LIF and FGF2 and the BMP protein antagonist Noggin.
FIG. 4C is a graph showing the neural colony forming ability of Smad4(−/−) and wildtype E14K ES cells.
FIG. 4D is a graph showing the neural colony forming ability of ES cells cultured in the presence of LIF alone or in the presence of LIF and exogenous mouse *Cerberus*-like (mCer-1) protein.

The secreted factor Cerberus is a potent neural inducer in Xenopus (Bouwmeester et al., 1996), [as is the mouse homologue Cerberus-like (Belo et al., 1997)] and acts by antagonizing BMP signaling (Pearce et al., 1999; Piccolo et al., 1999). To determine whether Cerberus can interfere with neural stem cell commitment in mammalian cells, we cultured primary ES cells in the presence of LIF in media containing supernatant collected from transiently transfected Neuro2a cell lines producing mouse Cerberus-like (mCer-1) protein. The presence of 20% (v/v) of mCer-1 supernatant in 0.5 ml serum-free media+LIF resulted in close to a 50% increase in the numbers of primary neural stem cell colonies generated, compared to control ES cell cultures containing equivalent propertiors of supernatant from cell lines similarly transfected with the backbone vector without the mCer-1 gene (FIG. 4). A similar increase in sphere colony formation was also observed when using supernatant collected form a transiently transfected COS7 cell line (data not shown). Again consistent with the default model, mCer-1-mediated inhibition of BMP signaling can enhance the frequency with which single ES cells differentiate into colony forming neural stem cells. More over ES derived neural colonies in the presence of mCer-1 enriched media but not in the presence of the control media, express Otx-1 (data not shown), indicating the mCER-1 also may anteriorize the neural colony cells. Wnt proteins are known to inhibit neural differentiation (Harland and Gerhart, 1997) and Cerberus can antagonize Wnt signaling (Piccolo et al., 1999). However, the effect of exogenous mCer-1 on neural colony formation was not greater than exogenous Noggin, and substantially less than the effect of a Smad4 mutation, suggesting that under these conditions additional Wnt antagonism may not be required for ES-derived neural colony formation.

EXAMPLE 5

Neural cell fate is rapidly established from ES cells in the absence of exogenous factors An analysis of neural cell differentiation from ES cells at an earlier time period in culture would facilitate a more accurate estimate of the number of ES cells that differentiate into neural cells.

It was predicted that if ES cells were acquiring a neural identity by default, they would express neural markers at very early stages during the culture period. To test this, ES cells (seeded at 10 cells/μl) were allowed to adhere to a poly-ornithine substrate and the proportion of ES cells that differentiated into neural cells after 24 hours in the absence of serum and LIF was determined. After 24 hours in culture, 69.9±4.6% of ES cells were non-viable in the absence of growth factors (estimated using trypan blue exclusion, n=4 separate culture wells). Therefore, in addition to TGFβ-related inhibition, the low frequency of ES cells differentiating into neural cells may be a result of extensive cell death in long-term culture assays. However, of the remaining 30% of viable cells, 82% were immunoreactive for the neuroepitnelial marker nestin in the absence of growth factors (FIG. 5A) Although, the percentage of viable cells after 4 hours was significantly greater (about 90%), the frequency of nestin$^+$ cells at this earlier time point was similar (70–80%). The majority of the nestin$^+$ cells had a relatively large, flattened and irregular morphology with prominent filamentous immunolabeling within the cytoplasm. A smaller subpopulation (51%) of the nestin$^+$ cells were also immunolabeled for the immature neuronal marker βIII-tubulin (51%) end NcuN (29%), many of which had a relatively small soma with very little perinucler cytoplasm, and evidence for thin cytoplasmic processes resembling leading and trailing processes of a bipolar neuronal morphology (FIG. 5B) The addition of LIF and FGF2 to these culture conditions did not significantly alter the percentage of ES cells that differentiated into neural cells. These data indicate that within 24 hours, ES cells may be competent to directly differentiate into neural cells at low cell densities and serum-free conditions in the absence of exogenous growth factors.

A second prediction that can be made from the default model of neural fate specification is that an increase in cell density will facilitate inhibitory intercellular communication (cells in close proximity) and attenuate the numbers of ES cells differentiating into neural cells. To test this, we cultured ES cells in identical conditions for 24 hours, but increased the cell density by 5-fold (to 50 cells/μl). At this relatively higher cell density, the proportion of nestin$^+$ cells was reduced from 82% to 40% (t=2.98, p<0.05) in absence of growth factors and from 70% to 51% (t=2.79, p<0.05) in LIF+FGF2. The proportion of βIII-tubulin$^+$ cells was reduced from 51% to 13% (t=4.07, p<0.05) in absence of growth factors and from 53% to 7% (t=5.63, p<0.05) in LIF+GF2 (FIGS. 5A, 5B). LIF+FGF2 did not affect the reduction in cells expressing the neural markers at higher cell densities (data not shown).

To exclude the possibility that a subpopulation of ES cells at the start of the 24-hour culture period were already committed to a neural fate, we tested whether ES cells just prior to culturing expressed the ICM/ES cell nuclear marker Oct-4, a POU transcription factor (Nichols et al., 1998). After ES cells were trypsinized from their feeder layers and washed in serum-free media, the cell suspension was fixed in 4% paraformaldehyde and allowed to adhere to a poly-ornithine substrate before immunolabeling with an anti-Oct-4 antibody. Using this method, all of the ES cells retained their rounded morphology and were immunoreactive for Oct-4 (localized to the nucleus), but none expressed nestin. As control, forebrain-derived sphere colony cells expressed nestin under this immunolabelling protocol, but were negative for Oct4 expression. Next, it was tested whether the remaining non-nestin immunoreactive population after 24 hours in our low-density cultures retained their ES cell identity. All of the non-nestin immunoreactive cells (17%) expressed nuclear Oct-4 at cell densities of 10 cells/μl (FIG. 5C). The Oct-4$^+$ cells had a rounded morphology with a thin rim of perinuclear cytoplasm that was distinct from the morphology of nestin$^+$ cells. Furthermore, we observed a trend toward an increase in nuclear Oct-4-immunoreactivity (up to 26%) when ES cells were cultured at a 5-fold higher cell density (FIG. 5C), which was inversely proportional to the relative decrease in nestin and βIII-tubulin expression at the same high cell densities. Thus, increased cell density inhibits neural cell differentiation and may facilitate the maintenance of ES cells in an undifferentiated state.

EXAMPLE 6

Neuronal differentiation is enhanced in Smad4$^{(-/-)}$ ES cells

To determine whether TGFβ signaling influences the extent to which ES cells adopt a neuronal phenotype in the short term differentiation assay, as it did the acquisition of the neural stem cell phenotype (see above), Smad4$^{(-/-)}$ ES cells were cultured at relatively high cell densities (50 cells/μl for 24 hours and double-immunolabeled for nestin and βIII-tubulin. Under these conditions, neuronal differentiation from wildtype ES cells is relatively low. The number of nestin$^+$ cells that differentiated form Smad4$^{(-/-)}$ ES cells after a 24 hour culture period increased slightly, but not significantly to 71% compared to 58% in the E14K wildtype control ES cells (FIG. 5D). However, a more substantial increase in βIII-tubulin$^+$ neurons (26%) was observed from the Smad4$^{(/)}$ ES cells, compared to the F14K control ES cells (10%; t=2.62, p<0.05), and a greater number of the Smad4$^{(-/-)}$ ES cells demonstrated a more elaborate neuritic morphology. Thus, at a relatively high cell density, inhibition of the BMP signaling pathway resembles increased cell dilution in its effectiveness in facilitating neural cell differentiation from ES cells.

EXAMPLE 7

ES-derived neural stem cell colonies contribute extensively to all embryonic tissues in chimeric mice Neural stem cells derived from the embryonic and adult central nervous system demonstrate neural multiline age potential (Weiss et al., 1996). Similarly, neural stem cells derived from ES cells generate progeny that are specified to a neural fate and differentiate into neurons and glia. To determine if neural stem cell colonies have a broader potential to generate non-neural lineages, we performed mouse chimeric analyses. ES cells introduced into a blastocyst or aggregated with a morula predominantly contribute to the epiblast of the developing embryo, whereas extraembryonic tissues are primarily of host origin (Beddington and Robertson, 1989). As mentioned previously, cells within ES-derived neural colonies (adhered for 24 hours) express the undifferentiated neural marker nestin throughout all stages of colony formation. It was further determined that within 14 μm cryosections of whole ES sphere colonies after 7 days in culture all of the cells appeared to express nestin, which is similar to nestin expression in sectioned forebrain derived neural stem cell colonies. However, no nuclear Oct4 expressing cells in ES sphere colony sections or forebrain colony sections (data not shown) were observed, suggesting that no cells within ES derived neural colonies maintained an undifferentiated ES cell phenotype.

Blastocyst-stage or morula-stage embroyos were used as hosts and neural stem cell colonies derived either from: (a) embryonic or adult forebrain tissue from mice harboring a ubiquitously expressed LacZ transgene (ROSA) (Friedrich and Soriano 1991) or a ubiquitously expressed green fluorescent protein transgene (GFP) (Hadjantonakis et al., 1998); or (b) ES cells harboring a yellow or cyan fluorescent protein transgene (YFP, CFP) (gifts from Drs. Hadjantonakis and Nagy). Approximately 92% (22/24) of the single YFP or CFP ES-derived colonies aggregated with morulas after 24 hours in vitro contributing to the ICM in normally developed blastocysts (FIG. 6A, inset) and had substantial contribution to all embryonic tissues in embryos recovered from pseudopregnant females at E9.5 (FIG. 6A). However, blastocyst injections of cells derived from E14.5 or adult ROSA neural colonies did not integrate into the ICM of the host embryos after 24 hours and in many cases tended to adhere to the host mural trophectoderm. Embryos recovered between E7.5 and E8.5 from these chimeras did not contain any LacZ$^+$ cells (0/19). Furthermore, E14.5 ROSA or E9.5 GFP neural stem cell colonies were unable to aggregate with morulas over a 24-hour period. Neural stem cell colonies were apparently unable to adhere to the host embryonic cells in the morula aggregates. Consequently, host morulae developed normally over the 24-hour culture period into healthy blastocysts while the sphere colonies remained outside of the embryo (FIGS. 6B, C). To test whether ES-derived sphere colonies (that readily adhere to morula cells) could facilitate the integration of colonies derived from the B9.5 forebrain, we cultured CFP ES colonies with GFP E9.5 colonies together with the host morula. In all cases, no F9.5 GFP colonies were observed to integrate (0/18), even though in many cases the CFP ES colonies did. These data suggest that ES derived neural stem cell colonies are competent to colonize many different tissues when exposed to an appropriate environment. However, this ability is only transient since neural stem cell colonies isolated from embryos in the earliest stages of neural development do not appear to have the same capacity (e.g. adhere to morula cells or integrate into ICM) to contribute to chimeric mice. Thus, the pluripotency of neural stem cells may only be evident in the earliest stages of the ES to neural transition, before the neural cells become more restricted.

EXAMPLE 8

Figure 5:
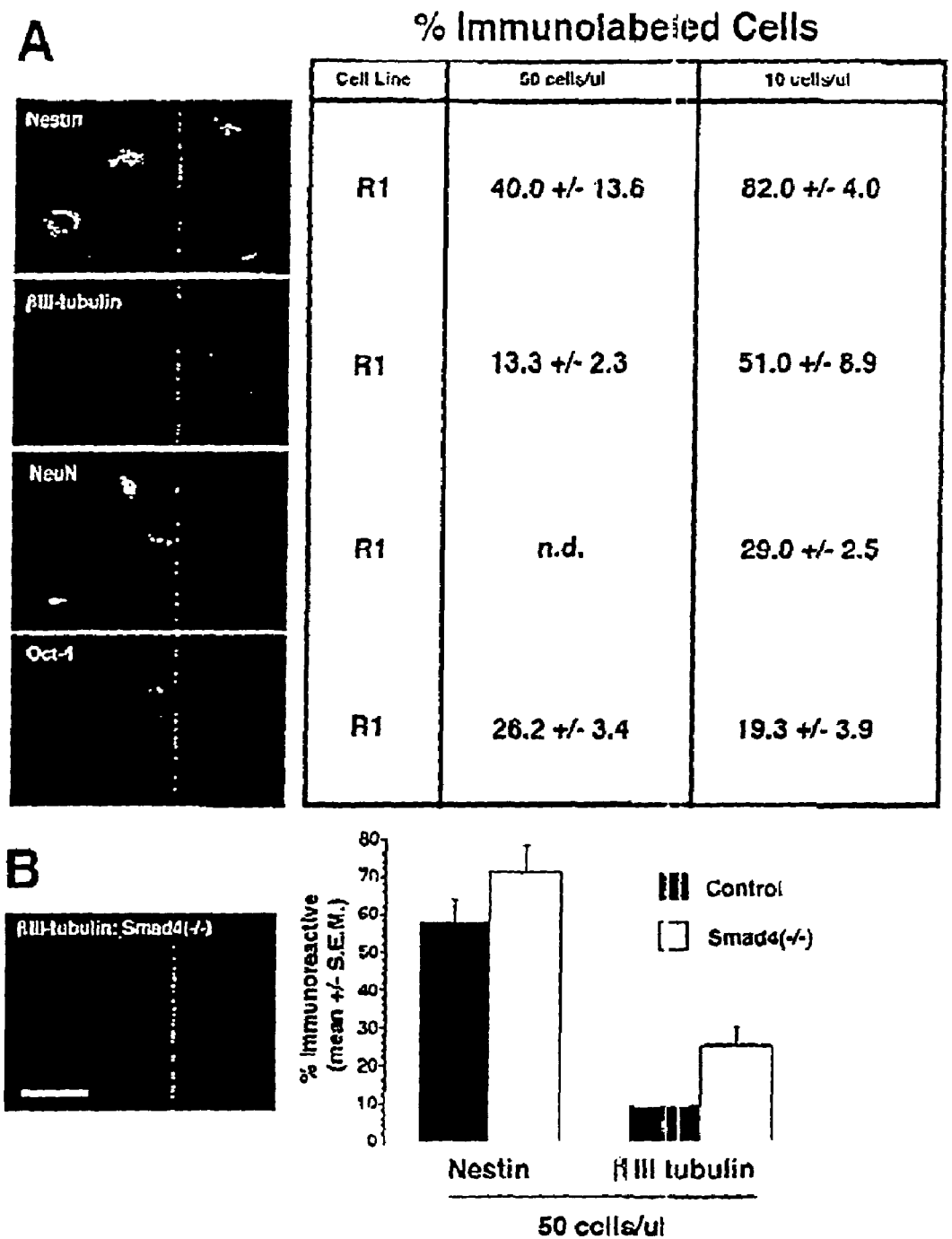
FIG. 5A is a table showing the proportion of ES cells cultured at low cell density that were immunoreactive or the neural precursor marker nestin, the immature neuronal marke βIII-tubulin, the marker NeuN, and ICM/ES cell nuclear marker Oct-4. The photographs at left shows ES cells immunocytochemically labelled for nestin. βIII-tubulin, NeuN., and Oct-4
FIG. 5B is a graph showing the proportion of either Smad4(−/−) or control E14K wildtype ES cells immunoreactive for the immature neuronal marker βIII-tubulin. The photograph at left shows Smad4(−/−) ES cells immunocytochemically labelled for βII-tubulin.

Undifferentiated ES cells and differentiated neural cells are distinct populations, even in high cell density, serum-containing cultures It is evident that even at high cell density some ES cells can start to express neural markers (e.g. FIG. 2B), raising the possibility that some of the Nestin expression we are detecting at low densities after 24 hours is normally present in undifferentiated ES cells at high densities. As reported above, morphologically distinct Nestin+ cells were separate from Oct4+ undifferentiated ES cells in serum-free, low-density conditions (FIG. 5). However, we further tested whether undifferentiated ES cells also expressed Nestin when cultured at high cell densities (~100 cells/ml) on a gelatin substrate in the presence of 15% FCS and LIF. After 24 hours in culture, many circumscribed undifferentiated ES cell colonies were observed, as well as separated cells distributed diffusely between the clusters. We found that the clusters of cells with the typical undifferentiated ES cell morphology do not express Nestin (FIGS. 7A, B). However, separate Nestin+ cells (16.1±3.4% of the cells per well) were observed between clusters and their morphology resembled Nestin+ cells from the low cell density cultures. In contrast, cells within the clusters expressed SSEA-1 (Solter and Knowles, 1978), an ES cell specific marker (65.3±3.9% of the cells per well) (FIGS. 7C, D). Importantly, the population of cells expressing SSEA 1 did not overlap with the population of cells expressing Nestin, confirming the results we obtained in serum-free, low-density conditions. These findings may indicate that there is a direct phenotypic change from ES cells to neural cells. This direct phenotypic change is substantially inhibited at high cell densities, confirming our earlier experiments. There were significantly fewer (t−9.3, p<0.05) Nestin+ cells in these high density cultures than the 32% Nestin+ cells seen in our low density ES cultures after 24 hours (see above), again confirming our previous results of inhibition of neural differentiation with increasing cell density after 24 hours.

It is possible that in the absence of a feeder cell substrate, some ES cells can escape neural inhibition especially in cell-sparse regions of the culture. To determine whether feeder cells can maximally inhibit the neural differentiation of ES cells, we cultured CFP ES cells on a feeder layer substrate at high cell densities in the presence of 15% FCS and LIF (our typical ES cell propagation and maintenance culture conditions). Greater than 98% viability of ES cells was observed when cultured under these conditions prior to immunostaining. Furthermore, the CFP ubiquitously expressed in the ES cells allowed us to unambiguously distinguish positive immunoreactivity between ES cells and feeder cells. Under these conditions, all of the CFP+ES cells expressed nuclear Oct4, but were negative for nestin expression. Similar results were observed using the SSEA-1 antibody. However, cells from embryonic forebrain derives sphere colonies cultured for two days on feeder cells were positive for nestin expression, but negative for Oct4 and SSEA-1 expression. Thus, under optimal culture conditions, ES cells maintain an undifferentiated ES cell phenotype and express ICM/ES specific markers, but do not express nestin. We conclude that in the absence of feeder-derived or serum-derived factors and at low cell densities, ES cells undergo a direct phenotypic change towards a neural fate, which is consistent with a default mechanism of neural fate specification.

DISCUSSION OF EXAMPLES 1–8

Neural cell fate specification during mammalian development

Once the primordium of the embryo proper is established (i.e. the segregation of ES cells in the ICM from extraembryonic tissues), the formation of the neural lineage is under inhibitory control. The present findings suggest that in isolation at relatively low cell densities, ES cells have an autonomous tendency to differentiate into neural cells, but that this tendency is partially mitigated by intercellular signals (stronger at higher densities) that inhibit neural differentiation. In vivo, where cell density and neural inhibition are maximal the differentiation of the neural stem cell lineage is highly dependent on the suppression of neural inhibition. In the foregoing examples, it was demonstrated that mouse ES cells adopt either a primitive neural stem cell fate or a neuronal cell fate in the absence of exogenous serum- or feeder layer-derived signals and in the absence of cell-to-cell contact in a low cell density, chemically-defined culture environment. Furthermore, blocking TCFβ-related signaling can augment the proportion of either neural stem cell colony formation or neuronal differentiation, consistent with similar neuronal differentiation evidence in a variety of vertebrate species (Sasai et al., 1995; Wilson et al., 1997; Fainsod et al., 1997; Hoodless and Hemmati-Brivanlou, 1997; Grinblat et al., 1998). It was also demonstrated that even at relatively low cell densities, ES cells secrete TGFβ-related neural inhibitors (e.g. BMP4) to limit the proportion of cells adopting a neural phenotype, a process that is similarly thought to occur in the epiblast during gastrulation in vivo (Beddington and Robertson, 1999). This may explain why a decrease in cell density did not increase the proportion of ES derived primitive neural stem cell colonies after 7 days. However, a cell density-dependent change in neural differentiation of ES cells was observed after 24 hours. It is possible that although these low-density conditions alleviate some neural inhibition (mediated primarily by TGFb signaling), colony forming primitive neural stem cells may be more sensitive to very low concentrations of TGFb. Thus, in the absence of all TGFb signaling (e.g. Smad4−/− ES cells), enhanced primitive neural colony formation is observed. Furthermore, if a default mechanism is solely responsible for neural stem cell fate specification, then other antagonists of neural inhibition in addition to TGFb inhibitors may be required under our culture conditions in order to maximally promote an ES-to-neural default. However, the findings also suggest that the default neutralization in mammalian cells may not be homologous with default neuralization in amphibian cells.

In *Xenopus*, ectodermal cells differentiate into epidermis as their alternate fate when neural differentiation is inhibited. Given that neural fate specification was assessed in totipotent ES cells, and while not wishing to be bound to any particular theoram, it was postulated that three possibilities exist for the acquisition of non-neural cell fates in this model. First, an alternate fate for ES cells under our defined culture conditions may be epidermis, which would indicate that mouse default neuralization is homologous with *Xenopus* default neuralization. Second, any non-neural cell type (including epidermis) may be established in a stochastic manner. Finally, an ES cell phenotype may be maintained in the absence of neural differentiation. These latter two possibilities would indicate that mouse default neuralization may be analogous, but not homologous, to *Xenopus* default neuralization. Again, while not wishing to be bound to any one theory, the results (FIG. 5) are consistent with the third possibility; the alternative to neural default for mouse. ES cells may be to maintain the undifferentiated ES cell fate. When cell density is increased in the 24 hour differentiation paradigm, the proportion of nuclear Oct-4 expressing ES cells increased, compared to the decrease in βIII-tubulin expressing neurons. Thus, although the establishment of a neural phenotype may be under inhibitory control (a default mechanism), additional signals may be required to drive ES cell differentiation into various non-neural lineages—signals that are likely to be absent or below threshold in the present culture conditions.

Recent evidence suggests that under the influence of a stromal cell line, ES cells can respond to neural inhibitors (in this case BMP4) by differentiating into epidermal cells (Kawasaki et al., 2000). These data suggest that the influence of the stromal cell line may facilitate ectodermal commitment in ES cells, which will then allow these cells to respond to neural inhibitors in a manner that is identical to amphibian ectodermal cells. Therefore, the alternative to a default neural cell fate may be dependent on the degree of commitment toward a particular lineage.

Both LIF and FGF are required for the initial transition of ES cells into neural colony forming stem cells. This raises the question of whether the functions of LIF and FGF are to induce neural stem cell differentiation of ES cells, which would not support the notion of neural fate being achieved autonomously. Although LIF and FGF are required for neural colony formation, the majority of ES cells can take on a neural identity within 24 hours in culture in the absence of any exogenous growth factors. Furthermore, the influence of Smad4 inactivation on neuronal differentiation (at relatively high densities) indicates that simply attenuating TGF-β-related signaling can promote neural specification under relatively inhibitory (high-density) conditions. Finally, preliminary experiments reveal that blocking extracellular FGF signaling using anti-FGF2 antibodies in relatively low cell density cultures does not appreciably decrease the percentage of nestin-expressing cells after 24 hours of differentiation in the absence of LIF. While not wishing to be bound by any one theory, the hypothesis that LIF and FGF (specifically FGF2) are acting permissively to specify a neural fate is supported by the results of targeted null mutations. For instance, the formation of neural tissue and subsequent early neural morphogenesis is relatively normal in mice lacking the LIF receptor (LIFR) (Li et al., 1995). Moreover, in the FGFR1 null mice (the primary receptor for FGF2), early gastrulation and neural tube formation was relatively normal (Yamaguchi et al., 1994). However, evidence for neural stem cell proliferation deficits in FGFR1$^{(-/-)}$ mice (Tropepe et al., 1999) as well as motor neuron differentiation deficits in LIFR$^{(-/-)}$ mice (Li et al., 1995) indicate that these factors are important for neural development at slightly later stages. Thus, again, not wishing to be bound by any one theory, we speculate that the primary roles for FGF and LIF are permissive ones and that ES cells autonomously adopt a neural cell fate. Our non-binding proposition is that LIF may initially maintain ES cell survival in these minimal culture conditions, whereas FGF may act primarily as a mitogen for neural stem and progenitor cell proliferation.

In contrast to the ICM and subsequent epiblast cells, ES cells can express the neural precursor marker nestin and the early neuronal marker βIII-tubulin within 24 hours when dispersed in culture in the absence of exogenous factors. The onset of nestin expression in vivo occurs at approximately E7.5 within the neuroepithelium of the presumptive neural plate (Lendahl et al., 1990) and neuronal differentiation begins thereafter. One possibility, which is merely a theory to which we do not wish to be bound, that emerges from our findings is that the potential for cells within the ICM or epiblast to behave like primitive neural stem cell sin vivo is actively suppressed. For example, epiblast cells in vivo may be competent to differentiate into neurons, but the absence of neurons prior to neurulation (even after a neural fate has been specified) suggests these cells may be inhibited from precocious neuronal differentiation. One intriguing non-binding theory is that the Notch signaling pathway may partially prevent neuronal differentiation by maintaining newly generated neural stem cells in an undifferentiated state. For example, functional inactivation of the mouse Su(H)/RBP-Jk gene, a downstream intracellular target of multiple Notch receptors, results in premature neuronal differentiation within the neural plate (de La Pompa et al., 1997). Similarly, functional inactivation of the mouse bHLH transcription factor HFS1 which negatively regulates neuronal differentiation via Notch activation, resulted in diminished forebrain neural stem cell self-renewal and a concomitant increase in neuronal differentiation (Nakamura et al., 2000).

Studies aimed at testing the role of BMP inhibition in neural fate specification using avian epiblast cells have come to different conclusions. BMP inhibition (by noggin orchordin) was not sufficient for ectopic neural cell differentiation in extraembryonic tissue (Streit et al., 1998; Streit and Stern 1999), and dissociated epiblast cells preferentially adopted a muscle cell phenotype in culture (George-Weinsein et al., 1996). Combinations of multiple BMP inhibitors, or BMP/Wnt inhibitors may be required for avian neural differentiation to occur. Both BMP an Wnt inhibition causes a more complete secondary axis to form in *Xenopus* transplantation experiments (Glinka et al., 1997). In addition, the generation of mice harboring targeted null mutations in both Noggin and Chordin, indicate that these two BMP inhibitors may function in concert to exert their effects on neural inhibition during mouse development (Bachiller et al., 2000). In the present study, mCer-1 (known to antagonize BMP, nodal and Wnt signaling) (Piccolo et al., 1999) was similarly effective at augmenting neural stem cell colony formation when compared to Noggin, suggesting that Wnt signaling alone may not actively suppress the ES to neural transition.

Cell density and culture media conditions employed in some check studies (George-Weinstein et al., 1996) indicate that the results may in fact be consistent with the neural default model. Although the epiblast cells were cultured at relatively low cell densities (~15 cells/µl), they were pretreated at high cell densities (~400 cells/µl) for up to 5 hours in the presence of serum and check embryo extract (George-Weinstein et al., 1996) a condition likely to suppress neural cell differentiation. Interestingly, these authors reported that neurofilament expressing check neurons, when present, were found in relatively cell-dispersed regions of the cultures, whereas muscle cells were typically aggregated. Thus, these data provide clear examples of how neural differentiation can be inhibited in epiblast cells upon aggregation.

A primitive stage in the neural stem cell lineage

The ontogenesis of tissue-specific mammalian stem cells is not well understood. In the present study we identified a novel cell type in the neural lineage based on the degree of neural commitment and growth factor responsiveness in vitro and the potential to give rise to neural and non-neural progeny in vivo. This cell type may be suitably described as a primitive neural stem cell. This term has been used previously to described a stem cell that is primarily tissue-specific, but that retains a certain degree of pluripotency during a restricted early period of development (Morrison et al., 1997).

With the exception of the hematopoietic stem cell (Weissman, 2000), our knowledge of the ontogeny of stem cells in other mammalian organ systems is comparatively limited. Clonal neural colonies generated from ES cells share similar features to clonal neural stem cell colonies described from the embryonic forebrain germinal zone. At a very low frequency (~0.2%), single ES cells proliferate in a LIF- and FGF-dependent manner to form neural colonies that express multiple neural precursor markers (e.g. nestin, Emx2 Hoxb1), even though the vast majority of ES cells up-regulate nestin expression and down-regulate nuclear Oct-4 expression within 24 hours. We previously demonstrated that the proportion of FGF-dependent neural stem cells isolated from nestin-expressing precursors of the E8.5 anterior neural plate was similar (~0.3%) (Tropepe et al., 1999), and forebrain neural stem cell colonies express similar region specific patterning genes (present study). Thus, the mechanism for segregating a subpopulation of colony-forming neural stem cells among a larger population of neural cells may be recapitulated during neural fate specification from ES cells. This raises the question of whether the first neural cell to arise in the nervous system is a neural stem cell or whether the first neural derivative is a general neural precursor cell that precedes (or is generated simultaneously with) the emergence of the neural stem cell lineage (van der Kooy and Weiss, 2000).

The ES cell-derived colonies are typically spheroid in morphology and many flat in suspension as has previously been described for neural stem cell-derived colonies at all ages (Reynolds and Weiss, 1996). ES cell-derived colonies do not retain ES cell characteristics (e.g. do not express *Brachyury* or Oct-4 protein), but are specified to a neural identity, retaining the expression of neural genes such as Emx2 and HoxB1. Furthermore, cells derived from the neural colonies can differentiate into neurons and glia, suggesting that the initial colony-forming cell had neural multilineage potential. However, neural stem cells derived from ES cells display other features than those derived from the embryonic forebrain, which may indicate an earlier primitive stage in the neural lineage.

Figure 7:
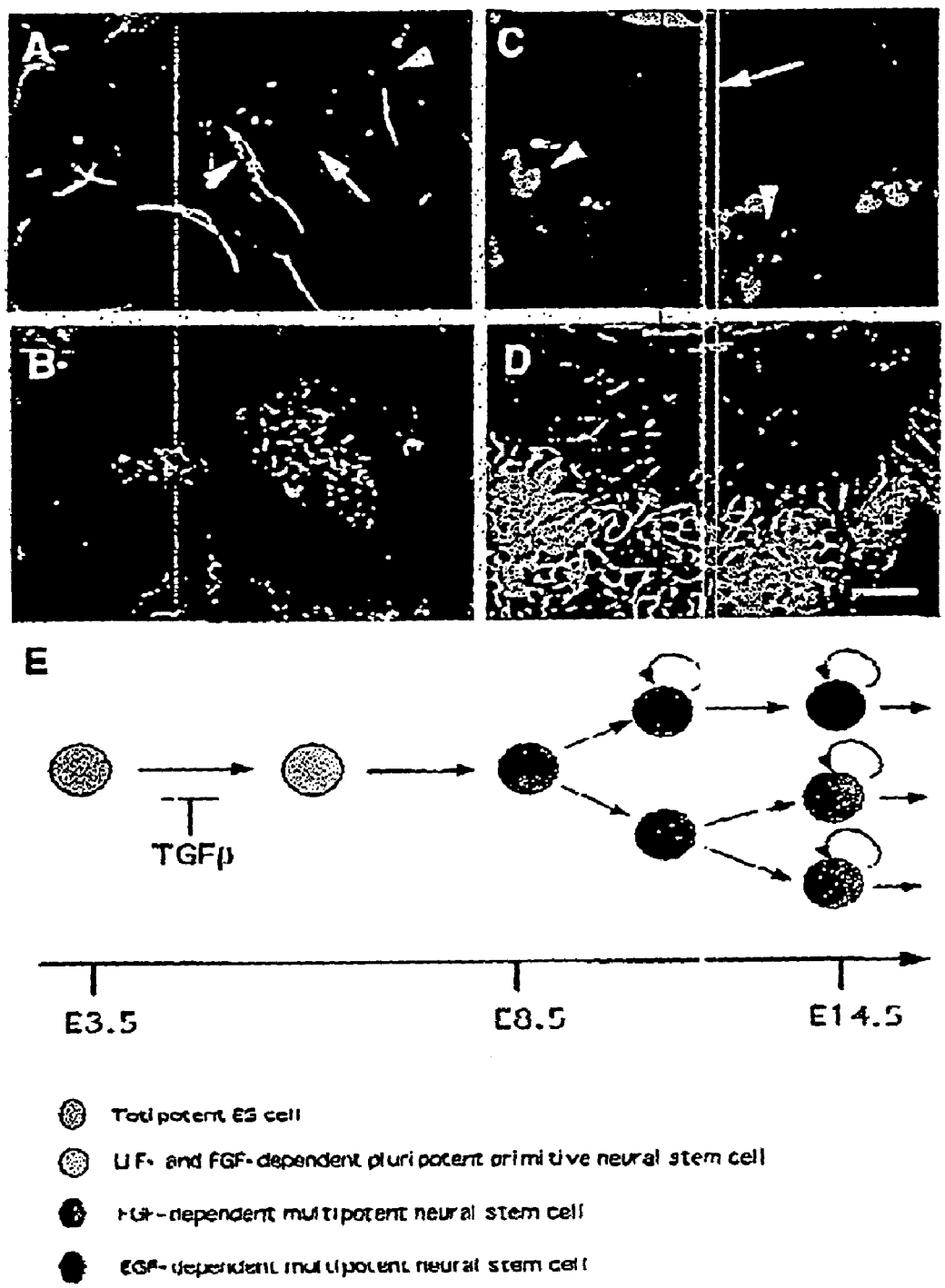
FIGS. 7A–D are photographs of well-circumscribed clusters of cells.
FIG. 7E is a diagram showing a model of the establishment of the early neural cell lineage from ES cells.

First, LIF and FGF are critical for ES-derived neural stem cell colony formation and subsequent subcloning (stem cell self-renewal). This is in contrast to neural stem cells isolated from embryonic or adult tissues, where either exogenous FGF or EGF is sufficient for colony formation and subcloning (Reynolds et al., 1992; Reynolds and Weiss, 1992). The nature of the LIF effect on the ES to neural transition is not completely understood. Although CNTF can substitute for LIF in maintaining ES cells in an undifferentiated state (Conover et al., 1993; Nichols et al., 1994), it does not substitute for LIF in promoting neural colony formation from ES cells, and LIF a one can not elicit neural colony formation from embryonic derived tissue. Thus, LIF does not appear to maintain neural colonies in an undifferentiated ES state or act as a mitogen. Instead, LIF may act as a survival factor (reviewed in Mehler and Kessler, 1997) that is initially required for ES cell viability. Subsequently, LIF can facilitate colony formation from early embryonic neural stem cells (presumably by keeping more stem cells alive longer), but it is not absolutely required. Hence, growth factor requirements may be sequentially modified form a primitive neural stem cell stage (LIF- and FGF-dependent) to an early embryonic neural stem cell stage (only FGF-dependent), and finally to a relatively mature neural stem cell stage where both FGF- and EGF-dependent subpopulations co-exist from late embryogenesis into adulthood (FIG. 7). A similar role has been attributed to LIF with respect to the survival of primordial germ cells in cultures. Congruent with our results, CNTF was not able to substitute for LIF in keeping primordial germ cells alive, even though embryonic germ cells (an ES-like cell derived from primordial germ cells) could be propagated with several members of the LIF family of ligands, including CNTF (Koshimizu et al., 1996). However, further studies will be required to determine more precisely the factors that mediate the transition form a LIF- and FGF-dependent primitive neural stem cell to a definitive FGF-dependent neural stem cell that can give rise to EGF dependent stem cells at later embryonic ages.

Second, the expression of neural genes and at least one non-neural gene (GATA4) indicates that the neural stem cell giving rise to neural colonies may retain a certain degree of pluripotency or primitive characteristics. Most important, this retained pluripotency can be observed in the ability of sphere colony derived cells to extensively colonize various embryonic tissues under appropriate influences in the chimeric embryos in vivo (no such pluripotency is shown by neural tube derived neural stem cells under similar conditions). Under the culture conditions employed in the present study the colony-forming neural stem cells derived from ES cells are specified, but not committed, to a neural fate.

Therefore, it has been identified a novel cell type in the neural lineage based on the degree of neural commitment and growth factor responsiveness in vitro and the potential to give rise to neural and non-neural progeny in vivo. This cell type may be suitably described as a primitive neural stem cell or a pre-neural stem cell, a term that has been used by others (Morrison et al., 1997) to describe a stem cell that is primarily tissue specific, but that retains a certain degree of pluripotency during a restricted early period of development.

Lineage restriction in developing neural stem cells may be reversible

To what extent can the microenvironment dictate the identify of neural stem cells and their ability to produce different progeny? We demonstrate that ES-derived primitive neural stem cells can produce progeny that colonize neural and non-neural tissues in chimeric mice in vivo. In contrast, we were unable to generate chimeras using neural stem cell colonies derived from either the early embryonic or adult forebrain. While not wishing to be bound to any one theory, this difference would suggest that primitive neural stem cells transiently retain their pluripotency, but though development neural stem cells become restricted in their ability to generate non-neural cell types. This restriction, however, may be reversible.

Clarke et al. (2000) recently demonstrated that a very low percentage (6 chimeras out of 600 viable embryos, or 1%) of adult neural stem cell colony cells could contribute to neural and non-neural tissues in a mouse chimera paradigm similar to the one we utilized in the present study. An increase in the frequency of chimeras was observed when undissociated stem cell colonies were injected into the mouse blastocoel or check amniotic cavity (Clarke et al., 2000). Consistent with our findings, the degree to which definitive neural stem cell-derived progeny (after isolation from embryonic or adult brain) can contribute to non-neural tissue in mouse is very restricted, compared to the proportion of ES cell derived primitive neural stem cell progeny that contribute to neural and non-neural tissues in the present study (22 chimeras out of 24 viable embryos, or 92%. However, it is clear from their analysis of the inductive influence of EB on adult neural stem cell colonies in vitro (to form muscle cells), that appropriate inductive signals can reveal some potential of neura stem cells to give rise to non-neural cells independent of the in vivo environment (Clarke et al., 2000). One intriguing possibility is that these inductive cues could enable some of the definitive neural stem cells to revert to a pluripotent primitive neural stem cell stage and subsequently produce progeny indicative of all three germ layers. Thus, the delineation of a pluripotent primitive neural stem cell stage during neural stem cell ontogeny may provide a basis for further understanding the mechanisms governing this remarkable cellular plasticity.

An ES cell paradigm for neural stem cell fate specification

Several studies have demonstrated neural differentiation from FR derived cells, with the addition of specific growth factors (Doetschmann et al., 1985; Bain et al., 1995; Fraichad et al., 1995; Strubing et al. 1995; Okabe et al., 1996; Brustle et al., 1999). Also BMP4 has been shown to suppress neuronal differentiation of EB derived cells (Finley et al., 1999). Although these observations clearly demonstrate the potency of such factor to promote or attenuate neuronal differentiation, each experiment initially utilized EB cultures in the presence of serum. Here we present an alternative and specific paradigm for neural cell fate specification directly from ES cells in serum-free conditions in the absence of EB formation. This paradigm can facilitate, for instance, the discovery of genes that positively and negatively regulate the transition from an ES cell to a neural cell by utilizing an expression-based gene trap library of ES cell lines (Stanford et al., 1998; Seaberg et al. 1999). Thus, our present findings underscore the potential for using ES cell models of mammalian neural development.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

FULL CITATIONS FOR REFERENCES REFERRED TO IN THE SPECIFICATION

Acampora, D., Avantaggiato, V., Tuorto, F., Briata, P., Corte, G., Simeone, A. (1988). Visceral endoderm-restricted translation of Otx1 mediates recovering of Otx2 requirements for specification of anterior neural plate and proper gastrulation. Development 125, 5091–5104.

Arceci, R. J., King, A. A. J., Simon, M. C., Orkin, S. H., Wilson, D. B. (1993), Mouse GATA-4: a retinoic acid-inducible GAIA-binding transcription factor expressed in endodermally derived tissues and heart Mol Cell. Biol. 13, 2235–2246.

Bachiller, D., Klingensmith, J., Kemp., C., Belo, J. A., Anderson, R. M., May, S. R., McMahon, J. A., McMahon, A. P., Harland, R. M., Rossant, J., De Robertis, E. M. (2000). The organizer factors chordin and noggin are required for mouse forebrain development. Nature 403, 658–661.

Bain, G., Kitchens, D., Yao, M., Huettner, J. E., Gottleib, D. I. (1995). Embryonic stem cells express neuronal properties in vitro. Dev. Biol. 168, 342–357.

Beddington, R. S. (1994). Induction of a second neural axis by the node Development 120, 613–620.

Beddington, R. S. P., Robertson, E. J. (1989). An assessment of the developmental potential of embryonic stem cells in the midgestation mouse embryo. Development 105, 733–737.

Beddington, R. S. P., Rashbass, P., Wilson, V. (1992). *Brachyury* a gene affecting mouse gastrulation and early organogenesis. Development *Supplement*, 157–165.

Beddington, R. S. P., Robertson, F. J. (1999). Axis development and early asymmetry in mammals. Cell 96, 195–209.

Bellows, C. G., Aubin, J. E. (1989). Determination of numbers of osteoprogenitors present in isolated fetal rat calvaria cells in vitro. Dev. Biol. 133, 8–13.

Belo, J. A., Bouwmeester, T., Leyns, T., Kertesz, L. Gallo, N., Follettio, M., De Robertis, E. M. (1997). *Cerberus*-like is a secreted actor with neuralizing activity expressed in the anterior primitive endoderm of the mouse gastrula. Mech. Dev. 68, 45–57.

Bouwmeester, T. Kim, S. H. Sasai, Y., Lu, B., DeRobertis, E. M. (1996). *Cerberus* is a head inducing secreted factor expressed in the anterior endoderm of Spemann's organizer. Nature 382, 595–601.

Brustle, O., Jones, K. N., Learish, R. D., Karram, K., Choudhary, K., Wiestler, O. D., Duncan, I. D., McKay, R. D. G. (1999). Embryonic stem cell-derived glial precursors: a source of myelinating transplants. Science 285, 754–756.

Chiasson, B. J., Tropepe, V., Morshead, C. M., van der Kooy, D (1999) Adult mammalian forebrain ependymal and subependymal cells demonstrate proliferative potential, but only subependymal cells have neural stem cell characteristics J. Neurosol. 19, 4462–4471.

Ciruna, B. G., Schwartz, L., Harpal, K., Yamaguchi, T. P., Rossant, J. (1997). Chimeric analysis of fibroblast growth factor receptor-1 (Fgfr-1) function: a role for FCFR1 in morphogenic movement through the primitive streak. Development 124, 2829–2841.

Clarke, D. L., Johansson, C. B., Wilbertz J., Veress, B., Nilsson, E., Karlstrom H., Lendahl, U., Frisen, J. (2000). Generalized potential of adult neural stem cells. Science 288, 1660–1663.

Conover, J. C., Ip, N. Y., Poueymirou, W. T., Bates, B., Goldfarb. M. P., DeChlara, T. M., Yancopoulos, G. D. (1993). Ciliary neurotrophic factor maintains the pluripotentiality of embryonic stem cells. Development 119, 559–565.

Coucouvanis, E., Martin, G. R. (1995). Signals for death and survival: a two-step mechanism for cavitation in the vertebrate embryo. Cell 83, 279–287.

Coucouvanis, E., Martin, G. R. (1999). BMP signaling plays a role in visceral endoderm differentiation and cavitation in the early mouse embryo. Development 126, 535–546.

Dani, D., Chambers, I., Johnstone, S., Robertson, M., Ebrahimi, B., Saito, M., Taga, T., Li, M. Burdon, T., Nichols, J., Smith A. (1998). Paracrine induction of stem cell renewal by LT-deficient cells: a new ES cell regulatory pathway. Dev. Biol. 203, 149–162.

de la Pompa, J. L., Wakeman, A. Correla, K. M., Samper, E., Brown, S., Aguilera, R. J., Nakano, T., Honjo, T., Mak, T. W., Rossant, J., Conlon, R. A. (1997). Conservation of the Notch signaling pathway in mammalian neurogenesis. Development 124, 1139–1148.

Doetschman, T. C., Eistetter, H., Katz, M., Schmidt, W., Kemler, R. (1985). The in vitro development of blastocyst-derived embryonic stem cell lines: formation of visceral yolk sac, blood islands, and myocardium, J. Embryol. Exp. Morphol. 87, 27–45.

Elefanty, A. G., Robb, L., Birner, R., Begley, C. G. (1997). Hematopoietic-specific genes are not induced during in vitro differentiation of sci-null embryonic stem cells Blood 90, 1435–1447.

Evans, M. J., Kaufman, M. H. (1981). Establishment in culture of pluripotential cells from mouse embryos. Nature 292, 154–156.

Fainsod, A. Deisler, K., Yelin, R. marom, K. Epstein, M. Pillemer, G., Steinbeisser, H., Blum, M. (1997). The dorsalizing and neural inducing gene follistatin is an antagonist of BMP-4, Mech. Dev. 63, 39–50.

Finley, M. F. A., Devata, S., Huettner, J. E. (1999). BMP-4 inhibits neural differentiation of murine embryonic stem cells, J. Neurobiol. 40, 271–287.

Friedrich, G., Soriano, P. (1991). Promotor traps in embryonic stem cells: a genetic screen to identify and mutate developmental genes in mice. Genes Dev. 5, 1513–1523.

Fraichard, A., Chassande, O., Bilbaut, G., Dehay, C., Savatier, P., Samarut, J. (1995). In vitro differentiation of embryonic stem cells into glial cells and functional neurons. J. Cell Sci. 108, 3181–3188.

George-Weinstein, M., Gerhart, J. Roed, R., Flynn, J., Callihan, B. Mattiacci, M., Miehle, C., Foti, G., Lash, J. W. Weintraub, H (1996). Skeletal cyogenesis; the preferred pathway of chick embryo epiblast cells in vitro. Dev. Biol. 173, 279–291.

Glinka, A., Wu, W. Onichtchouk, D., Blumenstock, C., Niehrs, C. (1997). Head induction by simultaneous repression of Bmp and Wnt signalling in *Xenopus*. Nature, 389, 517–519.

Godsave, S. F., Slack, J. M. W. (1989). Clonal analysis of mesoderm induction in *Xenopus laevis*. Dev. Biol. 134, 486–490.

Grinblat, Y., Gamse, J. Patel, M., Sive, H. (1998). Determination of the zebrafish forebrain: induction and patterning. Development 125, 4403–4416.

Grunz, H., Tacke, L. (1989). Neural differentiation of *Xenopus laevis* ectoderm takes place after disaggregation and delayed reaggregation without inducer. Cell Differ Dev. 28, 211–218.

Hadjantonakis, A. K., Gertsenstein, M., Ikawa, M., Okabe, M., Nagy, A. (1998). Generating green fluorescent mice by germline transmission of green fluorescent ES cells. Mech. Dev. 76, 79–90.

Harland, R., Gerhart, J. (1997). Formation and function of Spemann's organizer. Annu. Rev. Cell Dev. Biol. 13, 611–667.

Hommati-Brivanlou, A. Melton, D. A. (1992). A truncated activin receptor inhibits mesoderm induction and formation of axial structures in *Xenopus embryos*. Nature 359, 609–614.

Hemmati-Brivanlou, A., Melton, D. A. (1994). Inhibition of activin receptor signaling promotes neuralization in *Xenopus*. Cell 77, 273–281.

Hemmati-Brivanlou, A., Melton, D. A. (1997). Vertebrate neural induction. Annu. Rev. Neurosci. 20, 43–60.

Hoodless, P. A., Hemmati-Brivanlou, A. (1997). Inhibitory control of neural differentiation in mammalian cells. Dev. Genes Evol. 297, 19–28.

Hoppler, S., Brown, J. D., Moon, R. T. (1996). Expression of a dominant-negative Wnt blocks induction of MyoD in *Xenopus embryos*. Genes Dev. 10, 2805–2817.

Johansson, B. M., Wiles, M. V. (1995). Evidence for involvement of activin A and bone morphogenetic protein 4 in mammalian mesoderm and hematopoietic development, Mol. Cell Biol. 15, 141–151.

Kawasaki, H., Mizuseki, K., Nishikawa, S., Kaneko, S., Kuwana, Y., Nakanishi, S., Nishikawa, S-I, Sasai, Y. (2000). Induction of midbrain dopaminergic neurons from ES cells by stromal cell-derived inducing activity. Neuron 28, 31–40.

Kishimoto, T., Taga, T., Akira, S. (1994). Cytokine signal transduction. Cell 76, 253–282.

Koshimizu, U., Iaga, T., Watanabe, M., Saito, M., Shirayoshi, Y., Kishimoto, I., Nakatsuji, N. (1996). Functional requirement of gp130-mediated signaling for growth and survival of mouse primordial germ cells in vitro and derivation of embryonic germ (EG) cells. Development 122, 1235–1242.

Lamb, T. M., Knecht, A. K., Smith, W. C., Stachel, S. E., Economides, A. N., Stahl, N., Yancopolous, G. D. (1993). Neural induction by the secreted polypeptide noggin. Science 262, 713–718.

Lendahl, U., Zimmerman, L. B., McKay, R. D. G. (1990). CNS stem cells express a new class of intermediate filament protein. Cell 60, 585–595.

Li, M., Sendtner, M. Smith, A. (1995). Essential function of LIF receptor in motor neurons. Nature 378, 724–727.

Li, J., Ning, G., Duncan, S. A. (2000). Mammalian hepatocyte differentiation requires the transcription factor NHF4 (.Genes Dev. 14, 464–474.

Martens, D. J., Tropepe, V., van der Kooy, D. (2000). Separate proliferation kinetics of fibroblast growth factor-responsive and epidermal growth factor-responsive neural stem cells within the embryonic forebrain germinal zone. J. Neurosci. 20, 1085–1095.

Martin, G. R., Wiley, I. M., Damjanov, I. (1977). The development of cystic embryoid bodies in vitro from clonal teratocarcinoma stem cells. Dev. Biol. 61, 230–244.

Martin, G. R. (1981). Isolation of a pluripotent cell line from early mouse embryos cultured in medium conditioned by teratocarcinoma stem cells. Proc. Natl. Acad. Sci. USA 78, 7634–7638.

McGowan, K. M., Coulombe, P. A. (1998). Onset of keratin 17 expression coincides with the definition of major epithelial lineages during skin development. J. Cell Biol. 143, 469–486.

Mehler, M. F. Kessler, J. A. (1997). Hematolymphopoietic and inflammatory cytokines in neural development. Trends in Neurosci. 20, 357–365.

Mokry, J. Nemecek, S. (1998). Immunohistochemical detection of intermediate filament nestin. Actin Medica (Hradec Kralove) 41, 73–80.

Morrison, S. J., Shah, N. M. Anderson, D. J. (1997). Regulatory mechanisms in stem cell biology. Cell 88 287–298.

Nagy, A., Rossant, J. (1993). Production of a complete ES cell derived fetus. In *Gene targeting: a practical approach* (ed. A. L. Joyner), pp. 147–179. IRI. Press, Oxford, UK.

Nakamura, Y., Sakakibara, S-I., Miyata, T., Ogawa, M., Shimazaki, T., Weiss, S., Kageyama, R., Okano, H. (2000). The bHLH gene HES1 is a repressor of the neuronal commitment of CNS stem cells. J. Neurosci. 20, 283–293.

Nichols, J., Chambers, I., Smith A. (1994) Derivation of germline competent embryonic stem cells with combination of interleukin-6 and soluble interleukin-6 receptor. Exp. Cell Res 215, 237–239.

Nichols, J., Zevnik, B., Anastassiadis, K., Niwa, H., Klewe-Nebenius, D., Chambers, I., Schoeler, H. Smith, A. (1998. Formation of pluripotential stem cells in the mammalian embryo depends on the POU transcription factor Oct4. Cell 95, 379–391.

Okabe, S., Forssberg-Nilsson, K., Spiro, A. C., Segal, M., McKay, R. D. G. (1996). Development of neuronal precursor cells and functional postmitotic neurons from embryonic stem cells in vitro. Mech. Dev. 59, 80–102.

Oliver, G., Mailhos, A., Wehr, R., Copeland, N. G., Jenkins, N. A., Gruss, P. (1995). Six3, a murine homologue of the sine oculis gene, demarcates the most anterior border of the development neural plate and is expressed during eye development. Development 121, 4045–4055.

Oppenheimer, J. M. (1936). Structures developed in amphibians by implantation of living fish organizer. Proc. Soc. Exp. Biol. Med. 34, 461–463

O'Shea, K. S. (1999). Embryonic stem cell models of development. Anat. Rec. (New Anat.) 257, 32–41.

Pearce, J. J. H., Penny, G., Rossant, J. (1999). A mouse cerberus/DAN-related gene family. Dev. Biol. 209, 98–110.

Piccolo, S., Sasai, Y., Lu, B., De Robertis, E. M. (1996) Dorsoventral patterning in *Xenopus*: inhibition of ventral signals by direct binding of chordin to BMP4. Cell 86, 589–598.

Piccolo, S., Agius, E., Leyns, L., Bhattacharyya, S., Grunz, II., Bouwmeeser, T., De Robertis, E. M. (1999). The head inducer *Cerberus* is a multifunctional antagonist of Nodal, BMP and Wnt signals. Nature 397, 70–710.

Potten, C. S., Loeffler, M. (1990). Stem cells attributes, cycles, spirals, pitfalls and uncertainties. Lessons for and from the crypt. Development 110, 1001 1020.

Reynolds, B. A., Tetzlatt, W., Weiss, S. (1992). A multipotent EGF-responsive striatal embryonic progentor cell produces neurons and astrocytes. J. Neurosci. 12, 4565–4574.

Reynolds, B. A., Weiss, S. (1992). Generator of neurons and astrocytes from isolated cells of the adult mammalian central nervous system. Science 255, 1707–1710.

Reynolds, B. A., Weiss, S. (1996). Clonal and population analyses demonstrate that an EGF-responsive mammalian embryonic CNS precursor is a stem cell. Dev. Biol. 175, 1–13.

Sasai, Y., Lu, B., Steinbeisser, H., De Robertis, E. M. (1995). Regulation of neural induction by the Chd and Bmp-4 antagonistic patterning signals in *Xenopus*. Nature 376, 333–336.

Sato, S. M., Sargent, T. D. (1989). Development of neural inducing capacity in dissociated *Xenopus embryos*. Dev. Biol. 134, 263–266.

Seaberg, R. M., Tropepe, V., Stanford, W. L. Bernstein, A., van der Kooy, D. (1999). Neural determination genes revealed by expression trapping in embryonic stem cells. Soc. Neurosci. Abst. 25, 527.

Simeone, A., Gulisano, M., Acampora, D., Stornaiuolo, A., Rambaldi, M., Boncinelli, E. (1992). Two vertebrate homeobox genes related to the Drosophila empty spiracles gene are expressed in the embryonic cerebral cortex EMBO J. 11, 2541–2550.

Simeone, A., Acampora, D., Gulisano, M., Stornaiuolo, A., Boncinelli, E. (1992). Nested expression domains of four homeobox genes in developing rostral brain. Nature 358, 687–690

Sirard, C., De la Pompa, J. L., Elia, A. J., Itie, A., Mirtsos, C., Cheung, A. Hahn, S., Wakeham, A. Schwartz, L., Kern, E. E. Rossant, J. Mak, T. W. (1998). The tumor suppressor gene Smad4/Dpc4 is required for gastrulation and later for anterior development of the mouse embryo. Genes Dev. 12, 107–119.

Smith, A. G., Heath, J. K., Donaldson, D. D., Wong, G. G., Moreau, J., Sahl, M., Rogers, D. (1988). Inhibition of pluripotential embryonic stem cell differentiation by purified polypeptides. Nature 336, 688–690.

Smith, W. C., Knecht, A. K., Wu, M., Harland, R. M. (1993). Secreted noggin protein mimics the Spemann organizer in dorsalizing *Xenopus mesoderm*. Nature 361, 547–549.

Solter, D., Knowles, B. B. (1978). Monoclonal antibody defining a stage-specific mouse embryonic antigen (SSEA-1). Proc. Natl. Acad. Sci. USA 75, 555–5569.

Spemann, H. Mangold, H. (1924). Uber induktion von embryonaniagen durch implantation artfrender organisatoren. Arch. Mikr. Anat. EntwMech. 100. 599–638.

Stanford, W. L. Caruana, G., Vallis, K. A. Inadmdar, M. Hidaka, M., Bautch, V. L. Bernstein, A. (1998). Expression trapping: Identification of novel genes expressed in hematopoietic and endothelial lineages by gene trapping in ES cells. Blood 92, 4622–4631.

Streit., A., Lee, K. J., Woo, I., Roberts, C., Jessell, T. M., Stern, C. D. (1998). Chordin regulates primitive streak development and the stability of induced neural cells, but is not sufficient fro neural induction in the chick embryo. Development 125, 507–519.

Streit, A., Stern, C. D. (1999). Neural induction: a bird's eye view. Trends in Genet. 15, 20–24.

Strubing, C., Ahnert-Hilger, G., Shan, J., Wiedenmann, B, Hescheler, J., Wobus, A. M. (1995). Differentiation of pluripotent embryonic stem cells into the neuronal lineage in vitro gives rise to mature inhibitory and excitatory neurons. Mech. Dev. 53, 275, 287.

Taraviras, S., Monaghan, A. P., Schutz, G. Kelsey, G. (1994). Characterization of the mouse NHF-4 gene and its expression during mouse embryogenesis Mech Dev. 48, 67–79.

Rohyama, T. Lee, L. M.-Y., Rorke, L. B., Marvin, M., McKay, R. D. G., Trojanowski, J. Q. (1992). Nestin expression in embryonic human neuroepithelial tumor cells. Lab. Invest. 66, 303–313.

Tropepe, V., Sibilia, M., Ciruna, B. G., Rossan, J., Wagner, E. F., van der Kooy, D. (1999). Distinct neural stem cells proliferate in response to EGF and FCF in the developing mouse telencephalon. Dev. Biol. 208, 166–188.

van der Kooy, D., Weiss, S. (2000). Why stem cells? Science 287, 1439–1441.

Waddington, C. H., Schmidt, C. A. (1933). Induction by heteroplastic grafts of the primitive streak in birds. Roux's Arch. EntwMech. Org. 128, 522–563.

Weissman, I. L. (2000). Stem cells: units of development, units of regeneration and units of evolution. Cell 100, 157–168.

Wiles, M. V., Johansson, B. M. (1997). Anaysis of factors controlling primary germ layer formation and early hematopoiesis using embryonic stem cell in vitro differentiation. Leukemia 11(S3), 454–456.

Wilkinson, D. G. Bhatt, S., Cook, M., Boncinelli, E., Krumlauf, R. (1989). Segmental expression of Hox-2 homeobox-containing genes in the developing mouse hindbrain. Nature 341, 405–409.

Williams, R. L., Hilton, D. J., Pease, S., Willson, T. A., Stewart, C. L., Gearing, D. P., Wagner, E F., Metcalf, D., Nicola, N. A., Gough, N. M. (1988). Byeloid leukaemia inhibitory factor maintains the developmental potential of embryonic stem cells. Nature 336, 684–687

Wilson, P. A., Hemmati-Brivaniou, A. (1995). Induction of epidermis and inhibition of neural fate by Bmp-4. Nature 376, 331–333.

Wilson, P. A., Lagna, G., Suzuki, A., Hemmati-Brivanlou, A. (1997). Concentration-dependent patterning of the Xenopus ectoderm by BMP4 and its signal transducer Smad1. Development 124, 3177–3184.

Wrana, J. L. (2000). Regulation of Smad activity. Cell 100, 189–192.

Yamaguchi, T. P., Harpal, K., Henkemeyer, M., Rossant, J. (1994). fgfr-1 is required for embryonic growth and mesodermal patterning during mouse gastrulation. Genes Dev. 8, 3032–3044.

Zimmerman, L. B., De Jesus-Esobar, J. M., Harland, R. M. (1996). The Spemann organizer signal noggin binds and inactivates bone morphogenetic protein 4. Cell 86, 599–606

DETAILED DESCRIPTION OF THE FIGURES

FIG. 1. LIF-dependent neural cell colonies are clonally derived from single ES cells. (A) ES cells cultured at 20 cells/μl in chemically defined serum-free media proliferate to form sphere colonies in the presence of LIF (1000 U/ml). Photo inset shows a ES derived sphere colony after 7 days in culture (scale bar 100 μm). The addition of FGF2 (10 ng/ml) and heparin (2 (g/ml) causes a slight, but non-significant increase in the numbers of primary sphere colonies compared to LIF alone (t=1.1, p>0.05) or LIF+B27 (t–1.2, p>0.05. The presence of FGF2+heparin alone or B27 supplement alone (diluted to one-tenth the stock concentration: 1X) is not sufficient for colony formation. Data represent 6–12 cultures per group from 4–11 separate experiments. (B) Cells plated at limiting dilution in the presence of LIF revealed that the frequency in which at least one neural stem cell will proliferate to form a sphere colony (37% mark on the ordinal scale) was –0.2% (dashed line). Each data point represents the average of 6 cultures from 2 separate experiments. (C) Sphere colonies are composed of cells with neural precursor identify. After 3 days in vitro (relatively small) or 7 days in vitro (relative large) individual sphere colonies (n=6 from each of 2 separate experiments) were transferred to a poly-ornithine substrate and allowed to adhere for 24 hours. The expression of the neural precursor marker nestin was determined using immunocytochemistry. Scale bar 100 μm. (D) Neural colony forming ES cells displayed neural stem cell self-renewal characteristics. Single primary colonies generated in the presence of LIF alone (1a) were subcloned in LIF+FGF2, FGF2 or LIF to generate secondary colonies. Single primary colonies generated in the presence of LIF+FGF2+B27 (1b) were subcloned in LIF+FGF2+B27, FGF2+B27 or LIF+B27 to generate secondary colonies. Single secondary colonies generated in LIF+FGF2+B27 (2) were subcloned in LIF+FGF2+B27 to generate tertiary colonies. Single tertiary colonies generated in LIF+FGF2+B27 (3) were subcloned in LIF+FGF2+B27 to generate quaternary colonies. Single sphere colonies from primary culture (n=6–24 isolated colonies per condition form at least 2 separate experiments) were dissociated into a single cell suspension after 7 days in vitro and re-cultured. Secondary colonies derived from single primary colonies were quantified after 7–10 days in vitro and a similar procedure was used to subclone secondary and tertiary sphere colonies. LIF (1000 U/ml). FGF2 (10 ng/ml), heparin (2 μg/ml), B27 supplement (1X).

Figure 2:
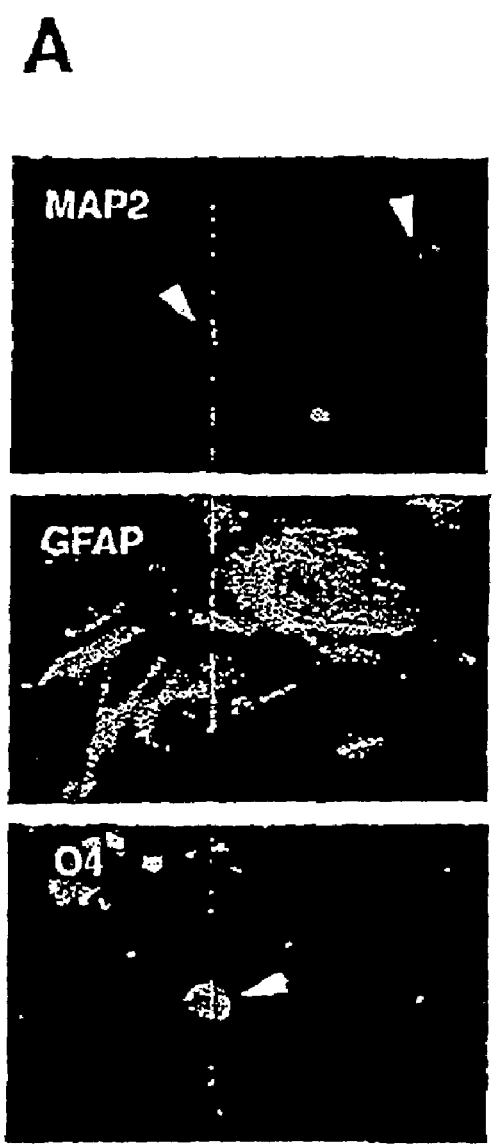
FIG. 2A shows inverted fluorescence microscope photographs of differentiated ES cell-derived sphere colonies, immunocytochemically labelled for neural cell-specific genes NAP2 (neurons), GFAP (astrocytes and O4 (oligodendrocytes).
FIG. 2B shows RT-PCR analysis of neural and non-neural lineage gene expression in RNA extracted from primary ES cells (R1). ES cell-derived sphere colonies (SC), and positive control tissue samples (+). Listed are the Emx2, HoxB1, Six3 and Otx1 markers for neural differentiation. *Brachyury* marker for mesoderm differentiation, GATA4 and HNF4 markers for endoderm differentiation, and CK-17 for epidermal differentiation.
Figure 2:
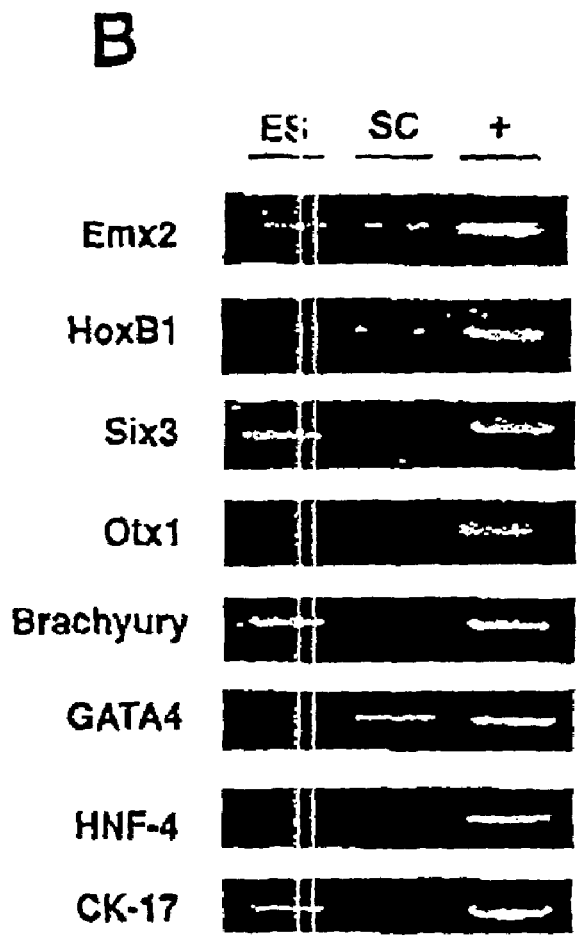

FIG. 2. Cells from ES-derived sphere colonies express neural specific genes and differentiate into neurons and glia. (A) Differentiated ES sphere colonies contain neurons (MAP2+, astrocytes (GFAP+) and oligodendrocytes (O4+, arrowhead). Data are representative of 18 cultures from 2–3 separate experiments. (B) Gene expression analysis using RT-PCR. RNA was isolated from sphere colonies after 7 days in vitro and analyzed for the expression of markers for neural differentiation [(Emx2 (151 bp), HoxB1 (325 bp), Six3 (571 bp), and Otx1 (128 bp)], endoderm differentiation [GATA4 (809 bp), HNF4 (629 bp)] mesoderm differentiation [*Brachyury* (857 bp)] and epidermis differentiation [cytokeratin-17 (CK-17) (833 bp)]. To normalize for the amount of cDNA present in the sample, the cDNA for GADPH (401 bp) was amplified. R1 refers to primary ES cells: SC refers to ES-derived sphere colony: + refers to positive tissue control (forebrain, hindbrain, somitic mesoderm, liver, skin). Data are representative of at least 3 separate experiments. Scale Bar: 20 mm.

Figure 3:
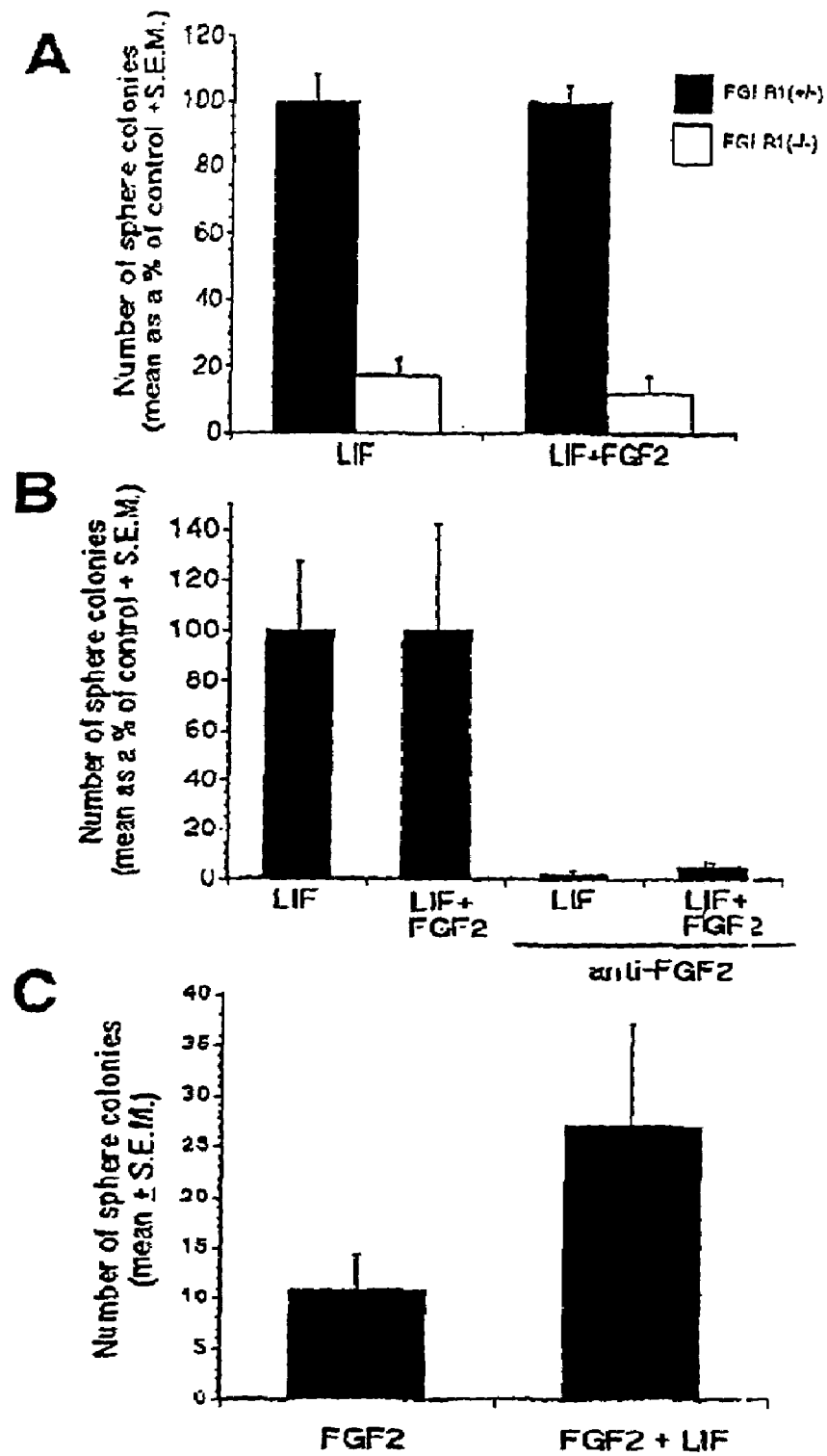
FIG. 3A is a graph showing the neural colony forming ability of ES cells with a homozygous null mutation (FGFR-1(−/−)) in the gene encoding FGF-receptor-1, or control heterozygous ES cells (FGFR-1(+/−)).
FIG. 3B is a graph showing the neural colony forming ability of ES cells cultured in the presence of anti-FGF2 antibodies.
FIG. 3C is a graph showing the neural colony forming ability of neural stem cells isolated from the day E9.5 forebrain and cultured in the presence of LIF and FGF2.

FIG. 3. Endogenous FGF-signaling mediates LIF-dependent primary neural colony formation. (A) Signaling through FGF-receptor-1 is required for neural colony formation. ES cells with a homozygous null mutation in the gene encoding FGF-receptor-1 (fgfr1Dtmk/fgfr1Dtmk) or control heterozygous ES cells (fgfr1Dtmk/+) were cultured at 20 cells/ml in LIF alone or LIF+FGF2+heparin and sphere colonies (n=12 cultures per group) were quantified after 7 days in vitro (t=8.5, p<0.05 comparing mutual and wildtype cells in LIF alone, t=8.9, p<0.05 comparing mutant and wildtype cells in LIF+FGF2). (B) Anti-FGF2 antibodies block neural colony formation. ES cells were cultured at 20 cells/ml in the presence of LIF or LIF+FGF2+heparin alone or in the presence of 1.25 mg/ml mouse monoclonal IgG anti-FGF2 antibodies. Data represent the average of 6 cultures per group from 23 separate experiments (t=3.66, p<0.05 comparing LIF alone in presence or absence of antibody; t=2.21, p<0.05 comparing LIF+FGF2 in presence or absence of antibody). (C) LIF facilitates colony formation in FGF2 from neural stem cells isolated from the E9.5 forebrain vesicles compared to FGF2 alone (t=2.9, p<0.05). Germinal zone tissue was cultured at 10 cells/ml in either FGF2+heparin or in the presence of FGF2+heparin and LIF and colonies were quantified after 7 days in vitro. Data represent the average of 6–9 embryos per group.

FIG. 4. TGFb/Wnt signaling can modulate neural stem cell differentiation from ES cells. (A) BMP4 inhibits neural colony formation compared to controls (t=4.45, p<0.05) ES cells were cultured at 20 cells/ml in the presence of LIF+FGF2+heparin alone or in the presence of BMP4. Sphere colonies were quantified after 7 days in vitro. Data represent the average of 6 cultures per group from 2 separate experiments. (B) Under similar conditions, Noggin (100 mg/ml) enhances neural colony formation compared to controls (t=4.78, p<0.05). Sphere colonies were quantified after 7 days in vitro. Data represent the average of 6 cultures per group from 2 separate experiments. (C) A null mutation in the Smad4 gene enhances neural colony formation compared to wildtype controls (t=2.67, p<0.05). Smad4(–/–) and wildtype E14K ES cells were cultured at 20 cells/ml in the presence of LIF and sphere colonies were quantified after 7 days in vitro. Data represent 6–12 cultures per group from 3–5 separate experiments. (D) mCer-I enhances neural colony formation compared to controls (t=2.4, p<0.05). ES cells were cultured at 20 cells/ml in the presence of LIF and B27 in the presence of 20% (v/v) in 0.5 ml culture wells of media supernatant from Neuro2a cell lines transiently expressing a mCer-I transgene of V2 plasmid control. Sphere colonies were quantified after 7 days in vitro. Data represent an average of 6 cultures per group from 2 separate experiments.

FIG. 5. Neural cell fate inhibition is attenuated in relatively low cell density cultures. ES cells were cultured on a poly-ornithine substrate for 24 hours at 50 cells/ml or 10 cells/ml in the absence of exogenous growth factors or, where indicated, in the presence of LIF+FGF2+heparin. (A) Cells expressing nestin, bIII-tubulin, NeuN and Oct-4. Cultures were counter labeled with Hoechst nuclear dye to facilitate cell quantitation. (B) In a similar manner, nestin and bIII-tubulin expression were assessed in Smad4(–/–) ES cells, compared to the E14K wildtype controls, plated at 50 cells/ml. Data represent the average proportion of phenotype-specific cells (positively immunolabeled) per total numbers of cells (Hoechst-labeled) obtained from 4–6 random standardized areas (using an ocular grid) at 20X objective magnification from 3–6 separate cultures. Scale bar: 20 mm. n.d., not determined.

Figure 6:
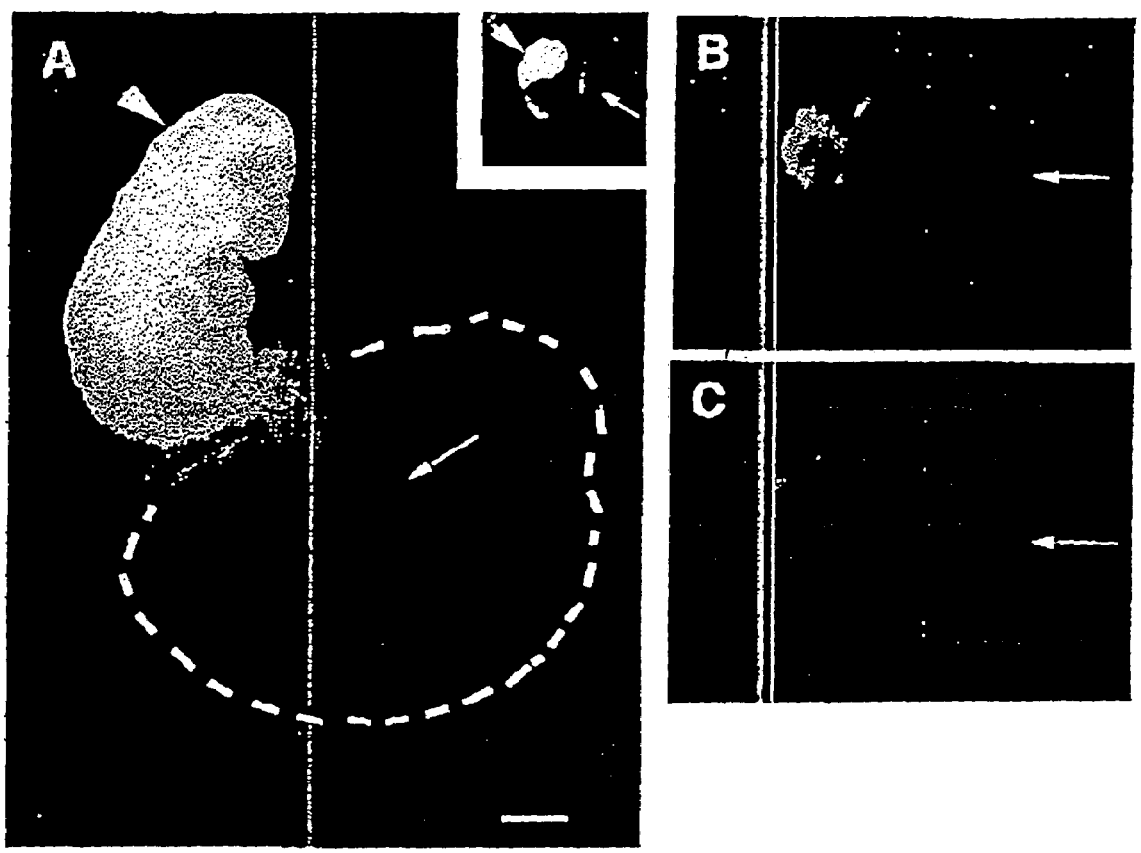
FIG. 6A shows an ultraviolet light microscope photograph of a chimeric day E9.5 mouse embryo generated using ES cell-derived neural colonies harbouring a yellow fluorescent protein transgene and a CD1 host morula. The inset shows a normally developed blastocyst after 24 hours in vitro from the aggregation of a yellow fluorescent protein ES cell neural colony and a CD1 host morula.
FIG. 6B shows a light microscope photograph of a mouse blastocyst (arrow) and an unintegrated day E9.5 telencephalon-derived sphere colony expressing green fluorescent protein, 24 hours after the attempted aggregation of the two.
FIG. 6C shows a light microscope photograph of the mouse embryo (arrow) developed from the blastocyst shown in FIG. 6B.

FIG. 6. ES-derived neural sphere colonies contribute extensively in mouse chimeras (A) Chimeric E9.5 embryo generated with a YFP ES sphere colony and a CD1 host morula. YFP-expressing cells are evident in all embryonic tissues (large arrow) and yolk sac (small arrow), but are absent from the placenta (outlined with dashed lines). Inset shows a normally developed blastocyst after 24 hours in vitro from the aggregation of a YFP ES sphere colony and a CD1 host morula. YFP cells integrate extensively into the ICM (large arrow), whereas the trophectoderm (faintly illuminated with a low intensity white light) is normally devoid of YFP cells (small arrow). (B) Twenty-four hours after the attempted aggregation of a GFP sphere colony derived from the E9.5 forebrain and a CD1 host morula, the morula develops normally into a blastocyst (arrow), while the sphere colony remains unintegrated outside of the embryo (both visualized with low intensity white light). (C) GFP-expressing cells were not observed within the embryo. Scale bar: 1 mm (A), 750 mm (A, inset), 250 mm (B, C).

FIG. 7. Undifferentiated ES cells do not express nestin at high cell densities. A small proportion of ES cells cultured at high cell densities (~100 cells/ml) on a gelatin substrate in the presence of LIF and 15% FCS display a relatively large flattened morphology and express nestin (arrowheads in A). In phase contrast images, these nestin positive cells are almost exclusively found between clusters of small rounded cells in areas of minimal cell to cell contact (arrowheads in B). The well-circumscribed clusters of cells, which do not express nestin (arrow in A and B) resemble typical undifferentiated ES cell colonies. These aggregated cells express the undifferentiated ES cell-specific marker SSEA-1 (arrowheads in C and D). Moreover, the relatively large cells that resemble nestin-positive cells do not express SSEA-1 (arrow in C and D). (E) A model depicting the establishment of the early neural lineage from ES cells. Totipotent ES cells derived from the E3.5 ICM directly differentiate (limited by the inhibitory control of TGFb molecules) to give rise to LIF- and FGF-dependent pluripotent primitive neural stem cells that undergo relatively few symmetric (expansionary) divisions. These primitive neural stem cells can generate neurons and glia, but under appropriate environmental conditions (chimeric embryos) have the potential to generate cells with the capacity to differentiate into various cell types. As development proceeds, primitive neural stem cells give rise to FGF-dependent (and not LIF dependent) neural stem cells that are present at the neural plate stage at E8.5. Tropepe et al., 1999). The FGF-responsive neural stem cells initially undergo mostly asymmetric divisions, but at later stages divide symmetrically to expand their population. By E14.5, FGF-responsive neural stem cells also give rise to a relatively separate EGF-responsive neural stem cell population, both of which have the potential to generate neurons and glia (Tropepe et al., 1999; Martens et al., 2000). Scale bar 40 mm.

We claim:

1. A method for differentiating one or more pluripotent mammalian embryonic stem (ES) cells comprising:
   a. culturing the mammalian ES cells at low cell density in a serum-free and feeder-layer free media comprising leukemia inhibitory factor; and
   b. allowing said mammalian ES cells to differentiate to primitive neural stem cells.

2. The method according to claim 1 for differentiating mammalian embryonic stem cells to cells with markers characteristic of neural cells comprising:
   a. culturing the mammalian embryonic stem cells in the serum free and feeder-layer free media at low cell density wherein said density is selected to minimize ES cell aggregation or embrvoid body (EB) formation; and
   b. allowing said mammalian ES cells to differentiate to primitive neural stem cells.

3. The method of claim 2 wherein the cell density is selected as to avoid EB formation.

4. The method of claim 1 wherein said cell density falls within the range of greater than 0 cells/µl to less than or equal to 50 cells/µl.

5. The method of claim 4 wherein the cell density falls within the range of greater than 0 cells/µl to less than or equal to 20 cells/µl.

6. The method of claim 5 wherein the cell density falls within the range of greater than 0 cells/µl to less than or equal to 10 cells/µl.

7. The method of claim 6 wherein the cell density is 10 cells/µl.

8. The method of claim 6 wherein there is no EB formation.

9. The method of claim 7 wherein the differentiating mammalian ES cells form at least one sphere colony.

10. The method of claim 1 wherein the differentiating mammalian ES cells form at least one sphere colony.

11. The method of claim 1 wherein the serum free media further comprises a cytokine.

12. The method of claim 1 wherein the primitive neural stem cells are pluripotent.

13. The method of wherein the serum free media further comprises a growth factor.

14. The method of claim 13 wherein the growth factor is selected from the members of the fibroblast growth factor (FGF) family of growth factor.

15. The method according to claims 14 wherein the growth factor is FGF2.

16. The method according to claim 1 wherein the media comprises Noggin or a compound from the *Cerberus* family of proteins.

17. A method for producing secondary mammalian primitive neural stem cell colonies comprising:
   a. culturing mammalian ES cells in low cell density serum-free and feeder-layer free media comprising leukemia inhibitory factor for a time and under conditions sufficient to differentiate the said mammalian ES cells to primary primitive neural stem cell colonies;
   b. dissociating and subcloning the primary primitive neural stem cell colonies generated from the said mammalian ES cells; and
   c. administering a growth factor or survival factor to the dissociated neural cells to produce secondary primitive neural stem cell colonies.

18. A method according to claim 17 wherein the growth factor is selected from among the members of the fibroblast growth factor (FGF) family of growth factors.

19. A method according to claims 18 wherein the growth factor is FGF2.

20. A method for screening for modulators of mammalian primitive neural stem cell differentiation comprising:
   a. culturing mammalian primitive neural stem cells in serum-free and feeder-layer free media comprising leukemia inhibitory factor under low cell density conditions in the potential modulator under conditions that produce differentiation in the absence of the potential modulator;
   b. detecting any differentiation of the cells and cell types generated, if any, in the presence of the modulator compared to differentiation and cell types generated in the absence of the potential modulator;
   c. determining whether the potential modulator affects the differentiation of the cells.

21. A method in accordance with claim 20, wherein the modulators comprise any culturing conditions that may modulate cellular, differentiation.

22. A method for screening for differentiation factors of cellular development comprising:
   a. culturing mammalian pluripotent embryonic stem (ES) cells in serum free media comprising leukemia inhibitory factor at low cell density in the presence of the differentiation factor;
   b. allowing the cells to differentiate;
   c. detecting differentiation of the cells, if any.

23. A method of claim 22 further comprising determining whether the differentiation of the cells comprises neural cell development.

24. A method for screening for differentiation factors of cellular development comprising:
   a. culturing the primitive neural stem cells produced by the method of claim 1 in serum free media comprising leukemia inhibitory factor, in the presence of the differentiation factor,
   b. detecting any differentiation of the cells.

25. The methbd of claim 24, wherein the media further comprises FGF2.

26. The method of claim 1 further comprising determining whether the mammalian ES cells differentiate into a homogenous uniform cell base.

27. The method of claim 1 further comprising determining whether the mammalian ES cells differentiate into a neural cell base.

28. A method for producing secondary mammalian primitive neural stem cell colonies comprising:
   a. culturing mammalian ES cells in low cell density serum-free and feeder-layer free media comprising leukemia inhibitory factor for a time and under conditions sufficient to differentiate the said mammalian ES cells to primary primitive neural stem cell colonies;
   b. dissociating and subcloning the primary primitive neural stem cell colonies generated from the said ES cells; and
   c. administering LW or B27 to the dissociated primary primitive neural stem cells to produce secondary primitive neural stem cell colonies.

29. The method of claim 1, wherein said primitive neural stem cell expresses at least one gene selected from the group consisting of nestin, GATA4, Emx2, and HoxB1.

* * * * *

SEQUENCE LISTING

<160> NUMBER OF SEQ ID NOS: 16

<210> SEQ ID NO 1
<211> LENGTH: 21
<212> TYPE: DNA
<213> ORGANISM: Artificial Sequence
<220> FEATURE:
<223> OTHER INFORMATION: Emx2: sense

<400> SEQUENCE: 1
gtcccagctt ttaaggctag a                                        21

<210> SEQ ID NO 2
<211> LENGTH: 23
<212> TYPE: DNA
<213> ORGANISM: Artificial Sequence
<220> FEATURE:
<223> OTHER INFORMATION: antisense

<400> SEQUENCE: 2
cttttgcctt ttgaatttcg ttc                                      23

<210> SEQ ID NO 3
<211> LENGTH: 19
<212> TYPE: DNA
<213> ORGANISM: Artificial Sequence
<220> FEATURE:
<223> OTHER INFORMATION: HoxB1: sense

<400> SEQUENCE: 3
ccggaccttc gactggatg                                           19

<210> SEQ ID NO 4
<211> LENGTH: 19
<212> TYPE: DNA
<213> ORGANISM: Artificial Sequence
<220> FEATURE:
<223> OTHER INFORMATION: antisense

<400> SEQUENCE: 4
ggtcagaggc atctccagc                                           19

<210> SEQ ID NO 5
<211> LENGTH: 20
<212> TYPE: DNA
<213> ORGANISM: Artificial Sequence
<220> FEATURE:
<223> OTHER INFORMATION: Otx1: sense

<400> SEQUENCE: 5
tcacagctgg acgtgctcga                                          20

<210> SEQ ID NO 6
<211> LENGTH: 20
<212> TYPE: DNA
<213> ORGANISM: Artificial Sequence
<220> FEATURE:
<223> OTHER INFORMATION: antisense

<400> SEQUENCE: 6
gcggcggttc ttgaaccaaa                                          20

<210> SEQ ID NO 7
<211> LENGTH: 20

```
<212> TYPE: DNA
<213> ORGANISM: Artificial Sequence
<220> FEATURE:
<223> OTHER INFORMATION: Six3: sense

<400> SEQUENCE: 7
cgcgacctgt accacatcct                                              20

<210> SEQ ID NO 8
<211> LENGTH: 20
<212> TYPE: DNA
<213> ORGANISM: Artificial Sequence
<220> FEATURE:
<223> OTHER INFORMATION: antisense

<400> SEQUENCE: 8
gccttggcta tcatacgtca                                              20

<210> SEQ ID NO 9
<211> LENGTH: 20
<212> TYPE: DNA
<213> ORGANISM: Artificial Sequence
<220> FEATURE:
<223> OTHER INFORMATION: Brachyury: sense

<400> SEQUENCE: 9
agtatgaacc tcggattcac                                              20

<210> SEQ ID NO 10
<211> LENGTH: 20
<212> TYPE: DNA
<213> ORGANISM: Artificial Sequence
<220> FEATURE:
<223> OTHER INFORMATION: antisense

<400> SEQUENCE: 10
ccggttgtta caagtctcag                                              20

<210> SEQ ID NO 11
<211> LENGTH: 20
<212> TYPE: DNA
<213> ORGANISM: Artificial Sequence
<220> FEATURE:
<223> OTHER INFORMATION: GATA4: sense

<400> SEQUENCE: 11
agcctacatg gccgacgtgg                                              20

<210> SEQ ID NO 12
<211> LENGTH: 20
<212> TYPE: DNA
<213> ORGANISM: Artificial Sequence
<220> FEATURE:
<223> OTHER INFORMATION: antisense

<400> SEQUENCE: 12
tcagccagga ccaggctgtt                                              20

<210> SEQ ID NO 13
<211> LENGTH: 21
<212> TYPE: DNA
<213> ORGANISM: Artificial Sequence
<220> FEATURE:
<223> OTHER INFORMATION: HNF-4: sense

<400> SEQUENCE: 13
```

```
ccatggtgtt aaaggacgtg c                                            21

<210> SEQ ID NO 14
<211> LENGTH: 20
<212> TYPE: DNA
<213> ORGANISM: Artificial Sequence
<220> FEATURE:
<223> OTHER INFORMATION: antisense

<400> SEQUENCE: 14
taggattcag atcccgagcc                                              20

<210> SEQ ID NO 15
<211> LENGTH: 20
<212> TYPE: DNA
<213> ORGANISM: Artificial Sequence
<220> FEATURE:
<223> OTHER INFORMATION: Primers for GAPDH: sense

<400> SEQUENCE: 15
accacagtcc atgccatcac                                              20

<210> SEQ ID NO 16
<211> LENGTH: 20
<212> TYPE: DNA
<213> ORGANISM: Artificial Sequence
<220> FEATURE:
<223> OTHER INFORMATION: antisense

<400> SEQUENCE: 16
tccaccaccc tgttgctgta                                              20
```